United States Patent
Lauer

(10) Patent No.: US 11,458,234 B2
(45) Date of Patent: Oct. 4, 2022

(54) FLUID CASSETTE WITH ALIGNMENT LATCHING HAVING AN IMPROVED TILT-TOLERANCE AS WELL AS A BLOOD TREATMENT APPARATUS

(71) Applicant: Fresenius Medical Care Deutschland GmbH, Bad Homburg (DE)

(72) Inventor: Martin Lauer, St. Wendel (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 284 days.

(21) Appl. No.: 16/587,486

(22) Filed: Sep. 30, 2019

(65) Prior Publication Data
US 2020/0023115 A1 Jan. 23, 2020

Related U.S. Application Data

(63) Continuation of application No. 15/126,244, filed as application No. PCT/EP2015/055299 on Mar. 13, 2015, now Pat. No. 10,471,196.

(30) Foreign Application Priority Data

Mar. 14, 2014 (DE) .......................... 102014103492.9

(51) Int. Cl.
*A61M 1/16* (2006.01)
*B01L 3/00* (2006.01)

(52) U.S. Cl.
CPC ............ *A61M 1/1621* (2014.02); *A61M 1/16* (2013.01); *B01L 3/00* (2013.01); *A61M 2205/12* (2013.01);
(Continued)

(58) Field of Classification Search
CPC .. A61M 1/1621; A61M 1/16; A61M 2205/12; A61M 2205/58; A61M 2209/08;
(Continued)

(56) References Cited

U.S. PATENT DOCUMENTS

| 4,436,620 | A | 3/1984 | Bellotti et al. |
| 4,479,762 | A | 10/1984 | Bilstad et al. |

(Continued)

FOREIGN PATENT DOCUMENTS

| CN | 1658916 | 8/2005 |
| CN | 102215888 | 10/2011 |

(Continued)

OTHER PUBLICATIONS

International Search Report in Application No. PCT/EP2015/055299, dated May 11, 2015, 11 pages (English Translation).

(Continued)

*Primary Examiner* — Benjamin R Whatley
*Assistant Examiner* — Jacqueline Brazin
(74) *Attorney, Agent, or Firm* — Fish & Richardson P.C.

(57) ABSTRACT

A fluid cassette, for example, a blood treatment cassette having a cassette body embodied as a hard part and, optionally, a film which is connected to the hard part and at least partially covers the hard part, wherein the hard part comprises at least one first alignment device, and a second alignment device which are optionally arranged at first and second opposite sides of the fluid cassette or are attached thereon. The disclosure relates in addition to a blood treatment apparatus.

13 Claims, 30 Drawing Sheets

(52) U.S. Cl.
CPC ... *A61M 2205/121* (2013.01); *A61M 2205/58* (2013.01); *A61M 2209/08* (2013.01); *B01L 2200/025* (2013.01); *B01L 2200/026* (2013.01)

(58) Field of Classification Search
CPC ..... A61M 2205/121; A61M 1/34; B01L 3/00; B01L 2200/025; B01L 2200/026
USPC ........................................................ 422/501
See application file for complete search history.

(56) References Cited

U.S. PATENT DOCUMENTS

| | | |
|---|---|---|
| 4,666,598 A | 5/1987 | Heath et al. |
| 4,770,769 A | 9/1988 | Schael |
| 5,470,483 A | 11/1995 | Bene et al. |
| 5,628,908 A | 5/1997 | Kamen et al. |
| 5,759,502 A | 6/1998 | Spencer et al. |
| 5,783,072 A | 7/1998 | Kenley et al. |
| 5,941,842 A | 8/1999 | Steele et al. |
| 6,001,228 A | 12/1999 | Huber et al. |
| 6,132,616 A | 10/2000 | Twardowski et al. |
| 6,471,855 B1 | 10/2002 | Odak et al. |
| 6,481,980 B1 | 11/2002 | Vandlik et al. |
| 6,542,761 B1 | 4/2003 | Jahn et al. |
| 6,645,166 B2 | 11/2003 | Scheunert et al. |
| 6,695,803 B1 | 2/2004 | Robinson et al. |
| 6,752,172 B2 | 6/2004 | Lauer |
| 7,488,301 B2 | 2/2009 | Beden et al. |
| 7,648,627 B2 | 1/2010 | Beden et al. |
| 7,935,074 B2 | 5/2011 | Plahey et al. |
| 8,142,653 B2 | 3/2012 | Beden et al. |
| 2002/0041825 A1 | 4/2002 | Scheunert et al. |
| 2002/0062109 A1 | 5/2002 | Lauer |
| 2003/0013834 A1 | 1/2003 | Slack et al. |
| 2003/0042181 A1 | 3/2003 | Metzner |
| 2003/0130607 A1 | 7/2003 | Delnevo et al. |
| 2003/0138349 A1* | 7/2003 | Robinson ............ A61M 1/0218 422/44 |
| 2003/0220607 A1 | 11/2003 | Busby et al. |
| 2004/0079707 A1 | 4/2004 | Smith et al. |
| 2004/0084647 A1 | 5/2004 | Beden et al. |
| 2004/0186416 A1 | 9/2004 | Caleffi |
| 2005/0017505 A1 | 1/2005 | Thilly |
| 2005/0028313 A1 | 2/2005 | Mainville |
| 2005/0045548 A1 | 3/2005 | Brugger et al. |
| 2005/0230292 A1 | 10/2005 | Beden et al. |
| 2005/0283132 A1 | 12/2005 | Stanus et al. |
| 2006/0079826 A1 | 4/2006 | Beden et al. |
| 2006/0155236 A1 | 7/2006 | Gara et al. |
| 2006/0195064 A1 | 8/2006 | Plahey et al. |
| 2006/0224099 A1 | 10/2006 | Hutchinson et al. |
| 2006/0237351 A1 | 10/2006 | Felding |
| 2006/0254982 A1 | 11/2006 | Kopperschmidt |
| 2006/0289360 A1 | 12/2006 | Delnevo et al. |
| 2007/0080063 A1* | 4/2007 | Kennedy ................ B01L 9/527 204/451 |
| 2007/0112297 A1 | 5/2007 | Plahey et al. |
| 2007/0208292 A1 | 9/2007 | Ferrari |
| 2007/0232980 A1 | 10/2007 | Felt et al. |
| 2007/0243990 A1 | 10/2007 | Kolenbrander et al. |
| 2007/0286756 A1 | 12/2007 | Jones et al. |
| 2008/0058712 A1 | 3/2008 | Plahey |
| 2008/0058727 A1 | 3/2008 | Domash et al. |
| 2008/0097283 A1 | 4/2008 | Plahey |
| 2008/0105600 A1 | 5/2008 | Connell et al. |
| 2008/0105601 A1 | 5/2008 | Ikeda |
| 2008/0208159 A1 | 8/2008 | Stanus et al. |
| 2008/0228125 A1 | 9/2008 | Brugger et al. |
| 2009/0105657 A1 | 4/2009 | Domash et al. |
| 2010/0087771 A1 | 4/2010 | Karakama et al. |
| 2010/0100034 A1 | 4/2010 | Wich-Heiter |
| 2010/0133153 A1 | 6/2010 | Beden et al. |
| 2010/0200486 A1 | 8/2010 | Gunther et al. |
| 2012/0000547 A1 | 1/2012 | Gronau et al. |
| 2012/0023246 A1 | 1/2012 | Castro et al. |
| 2012/0030921 A1 | 2/2012 | Haecker et al. |
| 2012/0080437 A1 | 4/2012 | Guenther et al. |
| 2012/0141197 A1 | 6/2012 | Lauer |
| 2012/0232469 A1* | 9/2012 | Medina ..................... F04B 9/02 604/28 |
| 2013/0075314 A1 | 3/2013 | Nikolic et al. |
| 2013/0079635 A1 | 3/2013 | Patrick et al. |
| 2013/0248629 A1 | 9/2013 | Brandl et al. |
| 2015/0165105 A1 | 6/2015 | Beden et al. |
| 2015/0202619 A1 | 7/2015 | Bransgrove et al. |
| 2015/0273471 A1 | 10/2015 | Manzella, Jr. et al. |
| 2017/0014566 A1 | 1/2017 | Childers et al. |
| 2018/0071447 A1 | 3/2018 | Gronau et al. |

FOREIGN PATENT DOCUMENTS

| | | | |
|---|---|---|---|
| CN | 102421466 | 4/2012 | |
| DE | 19837667 | 3/2000 | |
| DE | 10053441 | 5/2002 | |
| DE | 10224750 | 12/2003 | |
| DE | 102004011461 | 9/2005 | |
| DE | 102007018362 | 10/2008 | |
| DE | 102007042964 | 3/2009 | |
| DE | 102009008346 | 8/2010 | |
| DE | 102009012632 | 9/2010 | |
| DE | 102009012633 | 9/2010 | |
| DE | 102009024469 | 1/2011 | |
| DE | 102009036101 | 2/2011 | |
| DE | 102010003642 | 9/2011 | |
| DE | 102010032181 | 1/2012 | |
| EP | 0223580 | 5/1987 | |
| EP | 0611227 | 8/1994 | |
| EP | 0952858 | 11/1999 | |
| EP | 0980686 | 2/2000 | |
| FR | 2594340 | 8/1987 | |
| GB | 2110564 | 10/1982 | |
| JP | 62-005355 | 1/1987 | |
| JP | 2001-504374 | 4/2001 | |
| JP | 2002-177383 | 6/2002 | |
| JP | 2003-518964 | 6/2003 | |
| JP | 2003-533243 | 11/2003 | |
| JP | 2004-521707 | 7/2004 | |
| JP | 2005-508719 | 4/2005 | |
| JP | 2005-528168 | 9/2005 | |
| JP | 2008-531192 | 8/2008 | |
| JP | 2008-272440 | 11/2008 | |
| JP | 2010-188164 | 9/2010 | |
| JP | 2012-520089 | 9/2012 | |
| JP | 2012-520090 | 9/2012 | |
| JP | 2012-524563 | 10/2012 | |
| KR | 20-0408394 | 2/2006 | |
| KR | 2008-0009208 | 1/2008 | |
| TW | 200824731 | 6/2008 | |
| WO | WO 1995/017603 | 6/1995 | |
| WO | WO 02/102440 | 12/2002 | |
| WO | WO 03/101510 | 12/2003 | |
| WO | WO-03101510 A1 * | 12/2003 | .......... A61M 1/1621 |
| WO | WO 2005/044339 | 5/2005 | |
| WO | WO 2005/087290 | 9/2005 | |
| WO | 2006/122400 A1 | 11/2006 | |
| WO | WO 2008/011220 | 1/2008 | |
| WO | WO 2008/053262 | 5/2008 | |
| WO | WO 2009/033511 | 3/2009 | |
| WO | WO-2009033511 A2 * | 3/2009 | ............. A61M 1/14 |
| WO | WO 2008/099890 | 5/2010 | |
| WO | 2010/061866 A2 | 6/2010 | |
| WO | WO 2010/102784 | 9/2010 | |
| WO | WO 2010/102790 | 9/2010 | |
| WO | WO 2010/121819 | 10/2010 | |
| WO | WO 2011/015309 | 2/2011 | |
| WO | WO 2012/010323 | 1/2012 | |

(56) References Cited

FOREIGN PATENT DOCUMENTS

| WO | WO 2014/035471 | 3/2014 | |
| WO | WO-2014121216 A1 * | 8/2014 | ................ B01L 9/00 |

OTHER PUBLICATIONS

International Preliminary Report on Patentability in Application No. PCT/EP2015/055299, dated Sep. 14, 2016, 8 pages (English Translation).

* cited by examiner

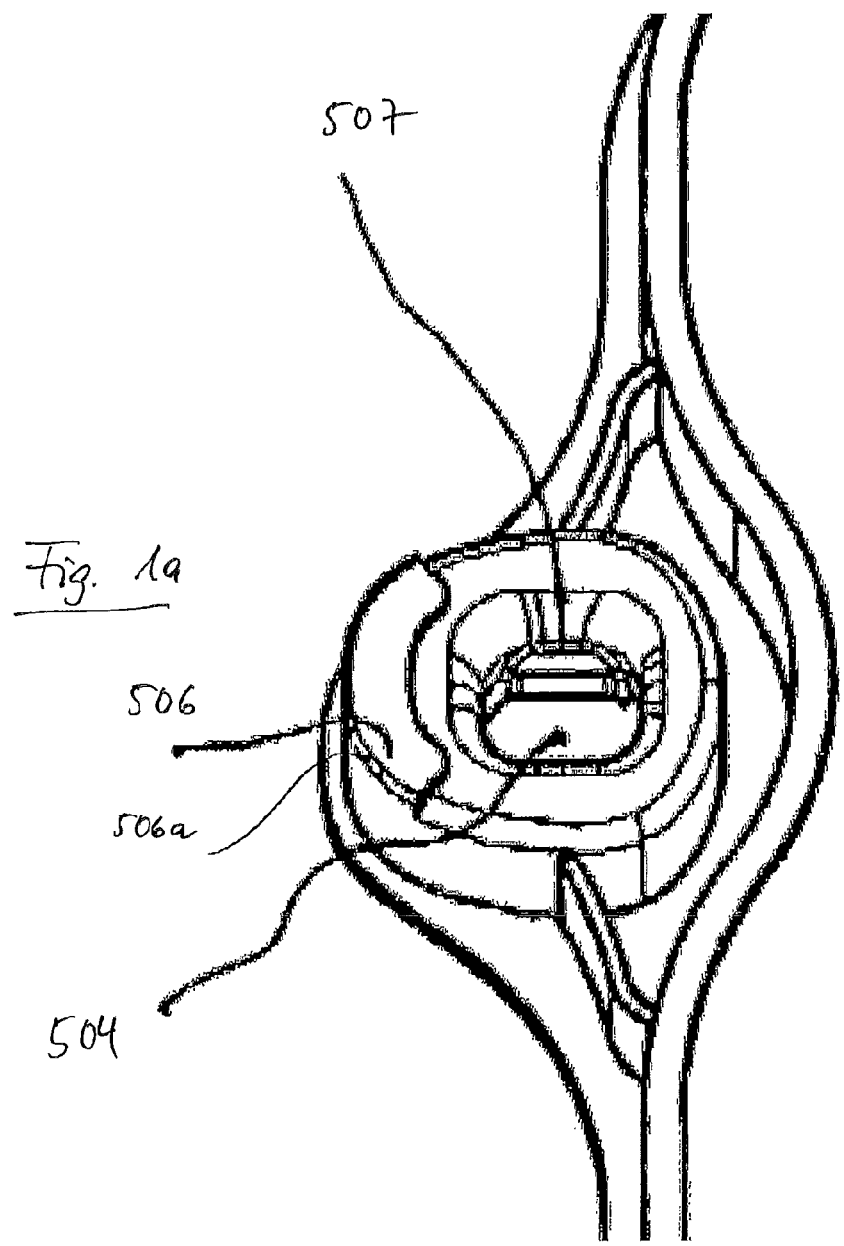

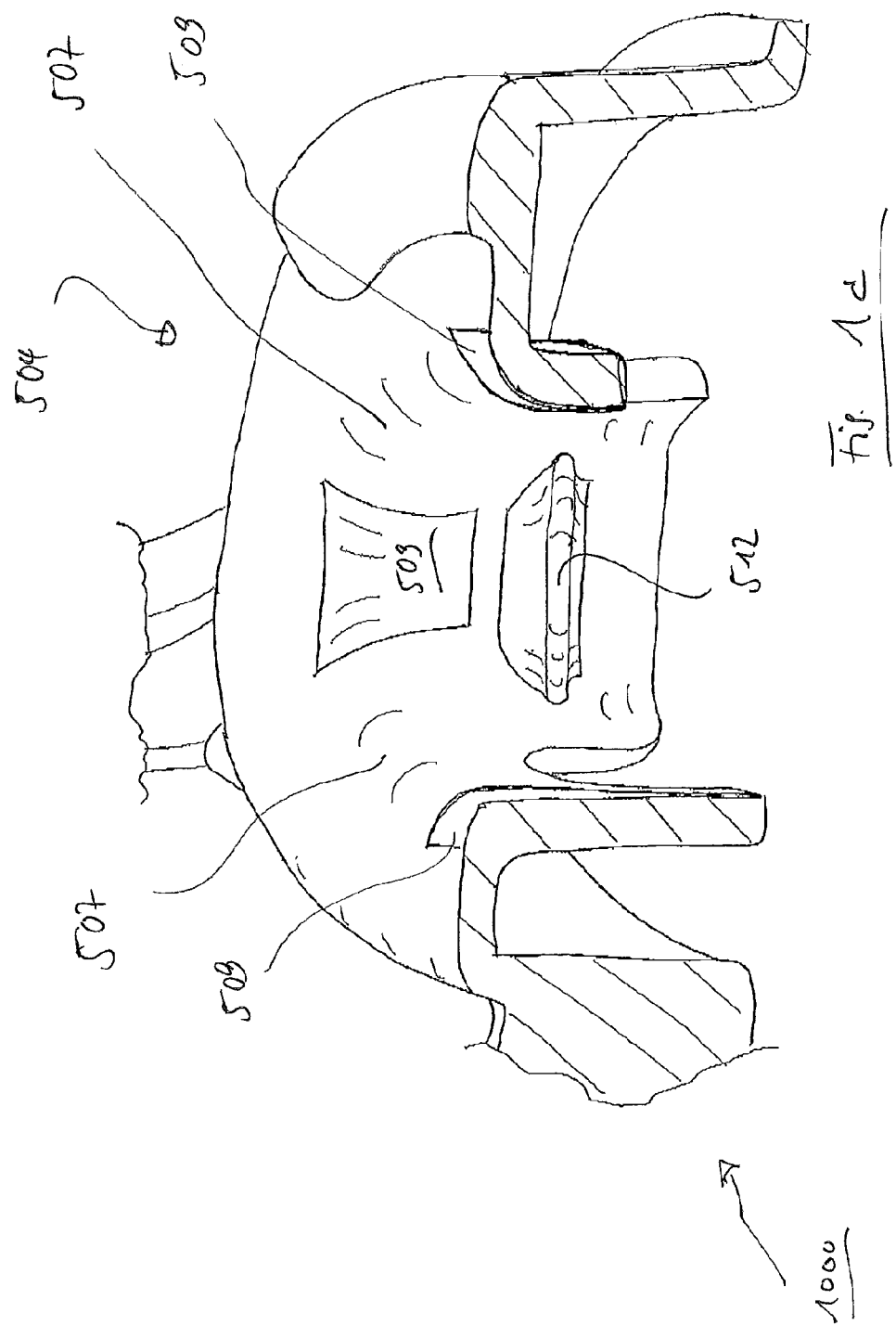

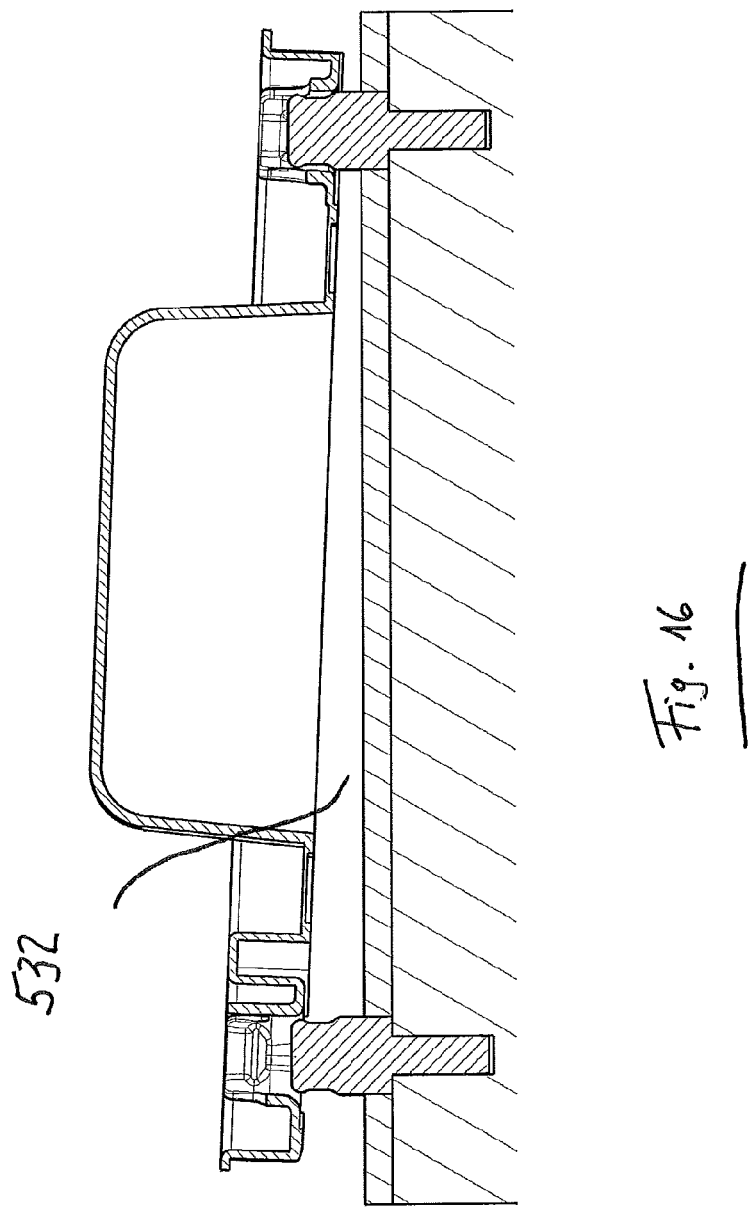

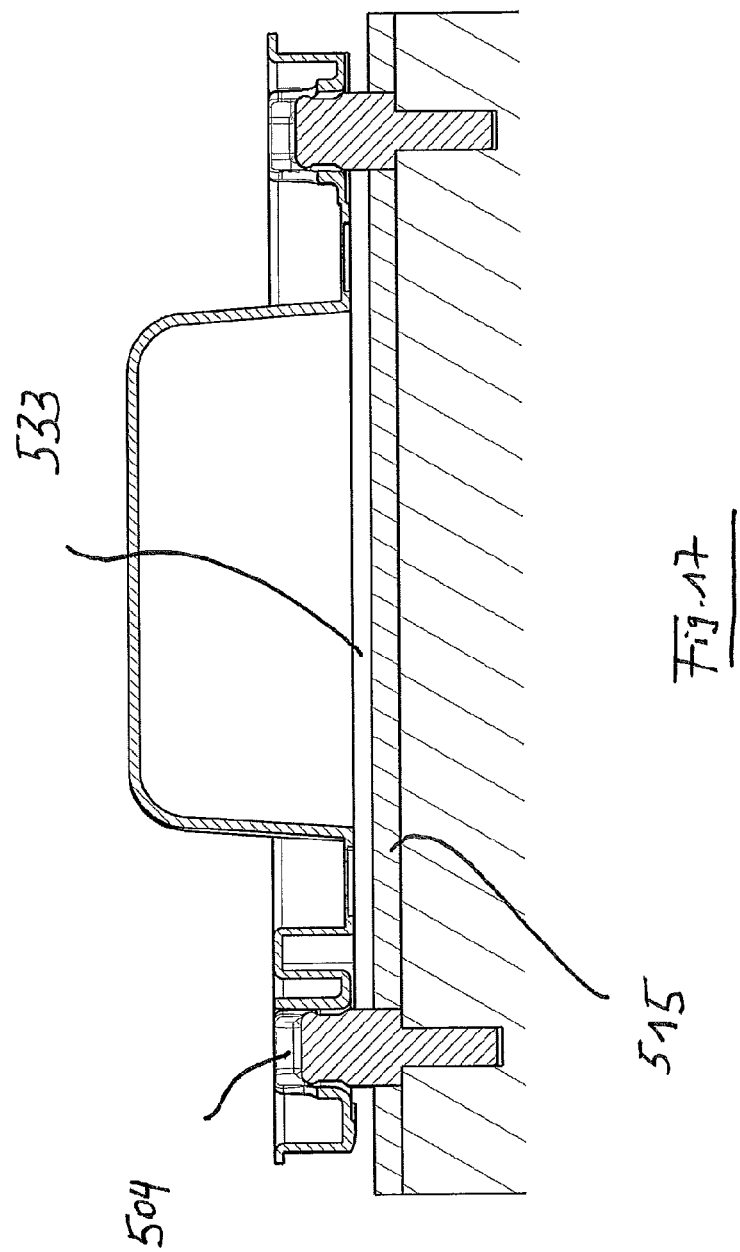

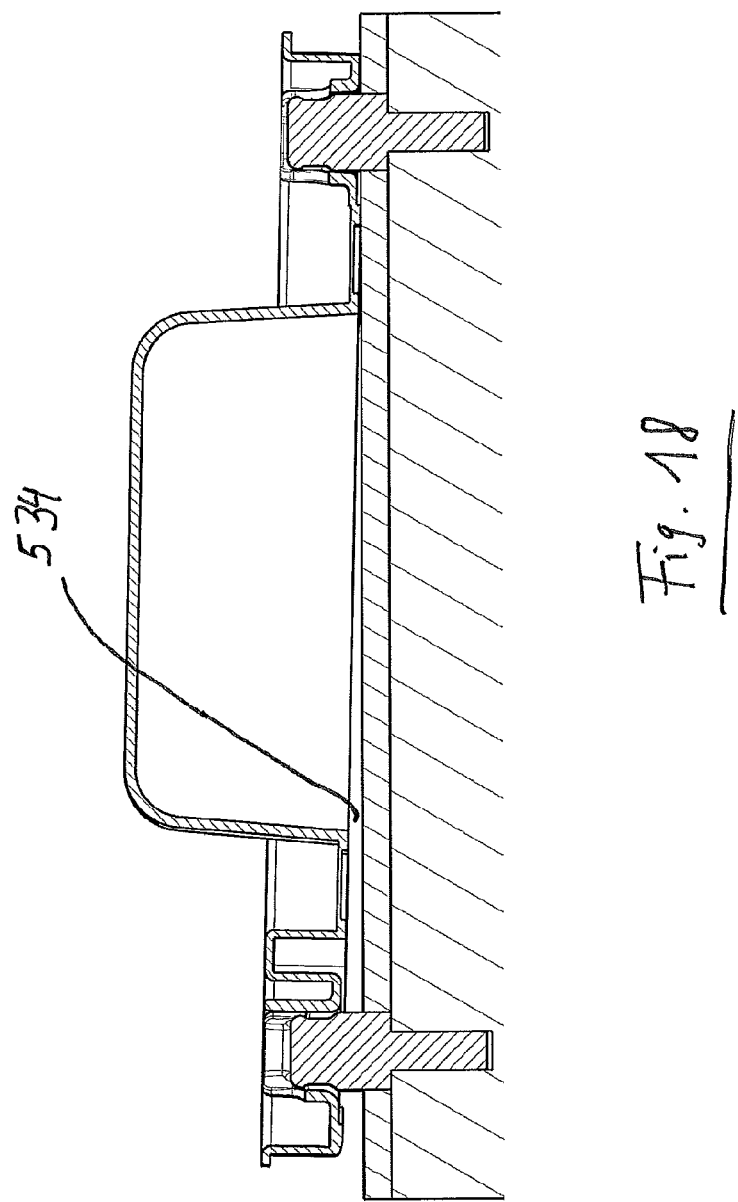

FLUID CASSETTE WITH ALIGNMENT LATCHING HAVING AN IMPROVED TILT-TOLERANCE AS WELL AS A BLOOD TREATMENT APPARATUS

CROSS REFERENCE TO RELATED APPLICATIONS

The present application is a continuation application of and claims priority to U.S. application Ser. No. 15/126,244, filed on Sep. 24, 2016, which is the national stage entry of International Patent Application No. PCT/EP2015/055299, filed on Mar. 13, 2015, and claims priority to Application No. DE 10 2014 103 492.9, filed in the Federal Republic of Germany on Mar. 14, 2014, the disclosures of which are expressly incorporated herein in its entirety by reference thereto.

TECHNICAL FIELD

This disclosure relates to fluid cassettes and blood treatment apparatuses.

Single-use systems are being increasingly used in the medical or laboratory technology as compact medical functional devices such as cassette systems or blood treatment cassettes in which liquids and gases, in particular medical fluids and blood, flow in passages and chambers. If they are provided for a single use, one speaks of disposable cassettes or single-use cassettes.

BACKGROUND

In most cases, these are hard-part film cassettes. The hard part consists regularly of an injection molding material such as PE, PP, PA, ABS, PMMA, PC or PVC. In the hard part, hose connections, connectors, chambers, passages and alignment devices are embodied by way of example. For using the blood treatment cassette, it is inserted into the blood treatment apparatus between a door and an actuator-sensor-unit of the blood treatment apparatus. By closing the door, it is brought into a so-called grouting or pressing position in which the film is pressed against the hard part and the blood treatment cassette together with the film are coupled in a spatially defined manner to the actuator-sensor mat of the actuator-sensor unit. When inserting the blood treatment cassette—also referred to as its equipping or as equipping of the apparatus—the main extension surface of the blood treatment cassette is adjusted and pressed or grouted against the main extension surface of the blood treatment apparatus (mostly the actuator-sensor mat). In the actuator-sensor mat and actuator-sensor plate (or unit), integrated actuators (components which are to be attached or connected to the actuator-sensor plate or mat, are also referred to herein as "actuator-sensor-sided") may be able to exercise movements through the film, through which, for example, pump or valve functions may be realized. Properties of fluids which flow through the blood treatment cassette may be measured by at least one sensor optionally provided on the actuator-sensor-plate.

SUMMARY

Aspects of this disclosure relate to medical fluid cassettes (cassettes for receiving medical fluid), such as blood treatment cassettes having a device for aligning the medical fluid cassettes (hereinafter, shortly as fluid cassette) at or on the medical treatment apparatus. Further, blood treatment apparatuses are described or specified that use the fluid cassette.

Although a blood cassette is mainly mentioned or referred to in the following, this is to be understood as merely one possible embodiment of the present invention. Whenever a blood cassette is mentioned herein, this is not to be understood as a restriction; rather it applies unchanged to a fluid cassette (according to the invention as well) even if it is not utilized for the treatment of blood.

In some embodiments, the fluid cassettes described herein, in particular a blood treatment cassette, have a cassette body embodied as a hard part. The blood treatment cassette may optionally comprise a film. If a film is provided, then it is connected to the hard part covering it at least partially. The hard part comprises at least a first alignment device and a second alignment device. They are preferably arranged on first and second opposite sides of the blood treatment cassette or are attached thereon.

Further, a blood treatment apparatus is described which is configured to be connected to the blood treatment cassettes as described herein. The blood treatment cassette comprises an actuator-sensor plate having at least one actuator. The latter is configured to interact between the actuators and/or sensors of the blood treatment apparatus and devices of the blood treatment cassette.

In all of the following embodiments, the use of the expression "may" or "may have", etc. is to be understood as a synonym to "is preferably" or "preferably has", etc. and it is to explain an exemplary embodiment.

Whenever numerical words are mentioned herein, the skilled person understands this as an indication of a numerically lower limit. As long as it does not lead to any discernible contradiction for the skilled person, the skilled person, therefore, implicitly reads for example in the indication "one" at all times as "at least one". This understanding is also encompassed by the present invention as well as the interpretation that, for example, "one" can alternatively be meant as "exactly one", as long as this is technically possible in the view of the skilled person. Both of which are encompassed by the present invention and apply to all used numerical words herein.

The herein given spatial information such as "top", "bottom", etc. refer to, in case of doubt, the representation shown in the here enclosed figures.

Embodiments may comprise one or more of the aforementioned or the following features in any arbitrary combination.

In certain exemplary embodiments, the blood treatment cassette comprises a front and/or rear side thereof, and at least one preferably closed edge bar with a front area. The front area lies in a plane which is preferably parallel to a main extension plane of the blood treatment cassette.

The front area in some exemplary embodiments is preferably flat. Hence, it is present in these embodiments in only one plane.

The main extension plane in some exemplary embodiments is parallel to a plane spanned from the film, if present, or is parallel to the main extension plane of the film.

In some exemplary embodiments, the blood cassette is embodied to be connected, during the intended use of the blood treatment cassette, in a translationally free of play manner with a first alignment pin of a blood treatment apparatus in the main extension plane. The second alignment device is embodied to be connected, during the intended use of the blood treatment cassette, in a rotatory free of play manner with the second alignment pin of the blood treatment apparatus about an axis that is preferably perpendicular or substantially perpendicular to the main extension plane.

In certain exemplary embodiments, the first alignment device comprises aligning facets whose alignment surfaces extend in a plane which is at least in portions, preferably perpendicular or substantially perpendicular, to the main extension plane of the blood treatment cassette. In some particular embodiments, the aligning facets touch the first alignment pin at least partially and preferably tangentially.

In some exemplary embodiments, the alignment facets comprise, completely or at least partially, edges curving up into an interior of a through-hole or opening of the first alignment device or are embodied as such.

In certain exemplary embodiments, an aligning facet is, at least partially, a portion of an insertion section, an insertion chamfer or an insertion funnel of an alignment device, wherein the insertion section, the insertion chamfer or the insertion funnel serve for receiving a section of the alignment pin. This section which is the aligning facet itself, has, exemplary or preferably, in at least one spatial direction or in two spatial directions perpendicularly to each other, a different curvature and/or inclination than other portions of the insertion section, the insertion chamfer or the insertion funnel or than adjacent portions of the insertion section, insertion chamfer or insertion funnel present on the same height, by way of example (with respect to an insertion direction or depth).

In some particular exemplary embodiments, an aligning facet is a portion of the insertion funnel or the insertion section in which the portion or the funnel has a larger inner diameter or a larger clearance diameter than on others and/or on the portions of the section or funnel adjacent to the aligning facet. The insertion funnel or insertion section comprises in some exemplary embodiments according to the present invention, for example, in a sectional view thereof, at least in part, a more or less distinctive funnel shape. Here, the insertion funnel opens out to an exterior of the alignment device and/or it gets narrower in direction of the adjacent pin.

The insertion funnel, the insertion section or the insertion chamfer may have an inwardly and/or an outwardly rounded inlet or edge (relative to the diameter of the insertion funnel or the insertion section, each in the area of the inlet). The rounding may be complete or present only in sections of the edge.

A latching edge is embodied in some exemplary embodiments as a contact surface area similar to an end-cutting area of pincers.

In certain exemplary embodiments, the first alignment device comprises at least one lifting edge bar. It may be present, relative to the center of the blood treatment cassette, on the outer edge of the first alignment device or may border the latter towards the lateral.

In some exemplary embodiments, the first alignment device and/or the second alignment device comprise each at least one actuator-sensor-sided insertion chamfer or at least one insertion funnel.

In certain exemplary embodiments, the first and/or second alignment devices comprise at least two snap-in tongues each having at least one latching edge. The latching edge extends thereby, preferably completely, substantially, or at least in section, in a plane parallel to the main extension plane of the blood treatment cassette.

In some exemplary embodiments, the through-hole or opening of the second alignment device is shaped substantially or entirely as a rectangle or an oblong hole.

In certain exemplary embodiments, the longitudinal axis of the second alignment device is oriented in the direction of the center of the through-hole or opening of the first alignment device.

In some exemplary embodiments, the blood treatment device is connected to a blood treatment cassette according to the invention.

In certain exemplary embodiments, a first alignment pin and/or a second alignment pin comprise an alignment diameter. Each or both comprise further a snap-in diameter which is less or smaller than the alignment diameter.

In some particular exemplary embodiments, a peripheral section of the alignment pin, present between the alignment diameter and a snap-in diameter, passes into the alignment diameter and/or the snap-in diameter by a rounded transition.

In certain exemplary embodiments, the first alignment pin and/or the second alignment pin comprise a flat front area.

In some exemplary embodiments, the first alignment pin and/or the second alignment pin comprise a rounded edge of the front area. The front edge is that edge at which the front area passes into the lateral surface or the peripheral surface of the alignment pin.

In certain exemplary embodiments, the first alignment pin and/or the second alignment pin have an alignment height, which is in the range of 0.1 to 0.5 times of their alignment diameter. The alignment height is the clear height or the height at which the alignment pin—preferably with or only with its alignment diameter, but not with its full height—rises above the level of the actuator-sensor mat surrounding it. The alignment diameter is the diameter of the alignment pin which adopts the aligning function of the alignment pin.

The alignment diameter may be the widest diameter of the portion of the alignment pin projecting over the actuator-sensor mat. It may be the diameter of the portion of the alignment pin which adjoins the latter directly above the actuator-sensor mat.

In some exemplary embodiments, the first alignment device and/or the second alignment device do not only serve for aligning but also for latching the blood treatment cassette to the blood treatment apparatus.

In certain exemplary embodiments, the machine door is preferably supported on the door-sided (that is on the machine side) support bars and on the flat front areas of the snap-in tongues.

In some particular exemplary embodiments, at least one aligning pin is embodied symmetric and/or as a cylinder. It comprises in these embodiments an aligning cylinder.

In some exemplary embodiments, all support surfaces of the machine door which contact the blood treatment cassette are, in a pressed condition, parallel to the main extension plane of the cassette. This advantageously ensures a sole alignment of the cassette through the alignment pins.

In certain exemplary embodiments, the alignment pins are embodied to guarantee, in connection with the flat front areas of the blood treatment cassette which are generously measured accordingly as well, an ergonomically favorable and admissible lateral misalignment or offset around both alignment devices of preferably 0.5 to 2.5 times of the alignment diameter or to limit this misalignment or offset thereto.

In some particular exemplary embodiments, the initial, admissible lateral misalignment of the blood treatment cassette is preferably within the 0.1 to 0.2 times of the alignment diameter before the respective insertion chamfers are engaged.

In certain exemplary embodiments, one of the alignment pins is present in one of the alignment devices, after the completion of a one-sided threading, in case threaded. One or more of the latching edges of the alignment device are therefore present at the rounded front-area edges of the alignment pin, while the other alignment pin has not yet started its threading or not yet completed it.

In certain embodiments, the blood treatment cassette is a disposable or a single-use item.

In certain embodiments, the blood treatment cassette and/or the blood treatment apparatus are configured for apheresis, hemodialysis, hemofiltration, hemodiafiltration, hemoultrafiltration and the like.

Some or all embodiments may comprise one or more of the above or the following advantages.

The free of play and repeatable arrangement of the blood treatment cassette, irrespective of its manufacturing tolerances and the tolerances of the blood treatment apparatus, may be considered as an achievable advantage.

A further advantage may be the possibility to take the blood treatment cassette, at any point or section, during equipping and removing despite the fact that the tilting constellations of each phase of equipping and removing are distinctive and proceed properly or as desired. An incorrect equipping or removing is therewith not possible in many embodiments described herein.

For a snap-in and snap out, only limited effort is required when equipping and removing, for example, less than 50 N.

Tilt-limited material stresses of the blood treatment cassette may advantageously be limited to values clearly below the limit where it may come to destruction or damage of the blood treatment cassette; this also applies to a jerky or sudden removal.

In some embodiments, an ergonomic and easy manual equipping and removing of the blood treatment cassette on the blood treatment apparatus may be guaranteed parallel to a free of play alignment and a destruction-proof arrangement. Incorrect strong tilting and any resulting stresses in the material may thereby be excluded. In the equipping and removing phases, the operator may grasp or take and load or press the blood treatment cassette at any point. Also, the snap-in and snap-out may be performed as desired in any order.

The free-of-play and maximum-high-alignment accuracy is advantageously achieved. Firstly: by providing two spaced-apart alignment devices, wherein the first alignment device defines the zero point of the translational displacement and the second alignment device, which is preferably embodied in a form of an oblong hole, determines the angular orientation and thereby balances the global dimension tolerances between the blood treatment apparatus and blood treatment cassette. Secondly, the state of the free of play is created through applying the aligning facets locally. Local as it is used here means that it concerns the tolerance attachment of the alignment diameter of the alignment pin to the faceted alignment holes or openings of the alignment devices (with much lower tolerances than the space between two alignment devices).

Due to the geometric design with point contact in connection with the elasticity of the blood treatment cassette material, the free of play state may be achieved in all tolerance positions without causing material damage or excessive equipping and removing efforts.

In the state of the art, the possibility of tilting and the associated material stresses and increases of the equipping and removing efforts up to dangerous levels is ensued due to the manual operation in connection with the free of play (or optionally without play) arrangements of the alignment devices on the alignment pins. To eliminate this problem or to minimize it according to the embodiments described herein, the following principles are being advantageously made use of:

In the process of equipping, the specified (edge) distances, heights—and diameter ratios according to the present invention advantageously ensure that all possible tilts between blood treatment cassette and blood treatment apparatus remain in angle ranges that lie below the critical tilt angle.

In the process of removing, the selected bending strength of the blood treatment cassette in connection with the distances of the alignment latching points to the detached edge bar of the blood treatment cassette and the aligning height of the alignment pins ensure that the tilting critical angle range, through the lifting effect on the edge bars, is not reached by one-sided prior snap-out. Rather, also the snap-out of the remaining alignment device is carried out shortly before.

When removing, the selected bending strength of the blood treatment cassette in connection with the less distance between the edge bar and the first alignment device, the selected alignment height and the tilted arrangement of the aligning facets of the second alignment device ensure that, in connection with the reduced lifting effect through tilted, one-sided snap-out in the maximum worst possible tilt direction, the critical tilt-angle-area may advantageously not be reached.

When removing, the selected bending strength of the blood treatment cassette in connection with the less distance from the edge bar to the second alignment device, the selected alignment height and the oblong-hole shaped design of the alignment through-hole or opening of the second alignment device ensure that, in connection with the reduced lifting effect through the tilted, one-sided snap-out in the maximum worst possible tilt direction, the critical tilt-angle-range may advantageously not be reached.

In the process of equipping and removing with any possible tilting, the snap-in diameter of the alignment pin determined to be smaller than the alignment diameter, in connection with its selected little overall height compared to the alignment height and to the distance between the alignment points, allows a sufficiently large tilt-uncritical tilt-angle-range.

When equipping and removing with any possible tilting, also in other not shown spatial directions, the flexible snap-in tongues and the cuts in connection with the mentioned dimensions of alignment pins and the selected edge bar distances advantageously permit a sufficiently large uncritical tilt-load tilt-angle-range.

A machine door and therewith a resulting pressing of the blood treatment cassette against the actuator-sensor unit are not absolutely necessary to ensure the illustrated inventive features. Already the free of play alignment and latching on the alignment pins may also, when utilizing blood treatment apparatuses which have no machine door, be sufficient for a reliable mounting and positioning of the blood treatment cassette.

BRIEF DESCRIPTION OF THE FIGURES

The present invention shall be exemplarily explained in the following by way of the accompanying drawings, in which identical reference numerals designate same or similar elements. In the partially simplified figures:

FIG. 1a shows an enlarged representation of a first section of FIG. 1a;

FIG. 1b shows an enlarged representation of a second section of FIG. 1a;

FIG. 1c shows an enlargement of a section of FIG. 1 in sectional view;

FIG. 2 is the representation of the blood treatment cassette of FIG. 1 after its rotation of 180° about a horizontal of FIG. 1;

FIG. 8 is the illustration of the blood treatment cassette of FIG. 1 after its rotation of 180° about a horizontal of FIG. 1;

FIG. 17 shows the fourth step of the equipping process, the double-sided termination of threading;

FIG. 18 shows the fifth step of the equipping process, the one-sided termination of an alignment latching;

DETAILED DESCRIPTION

Figure 1:
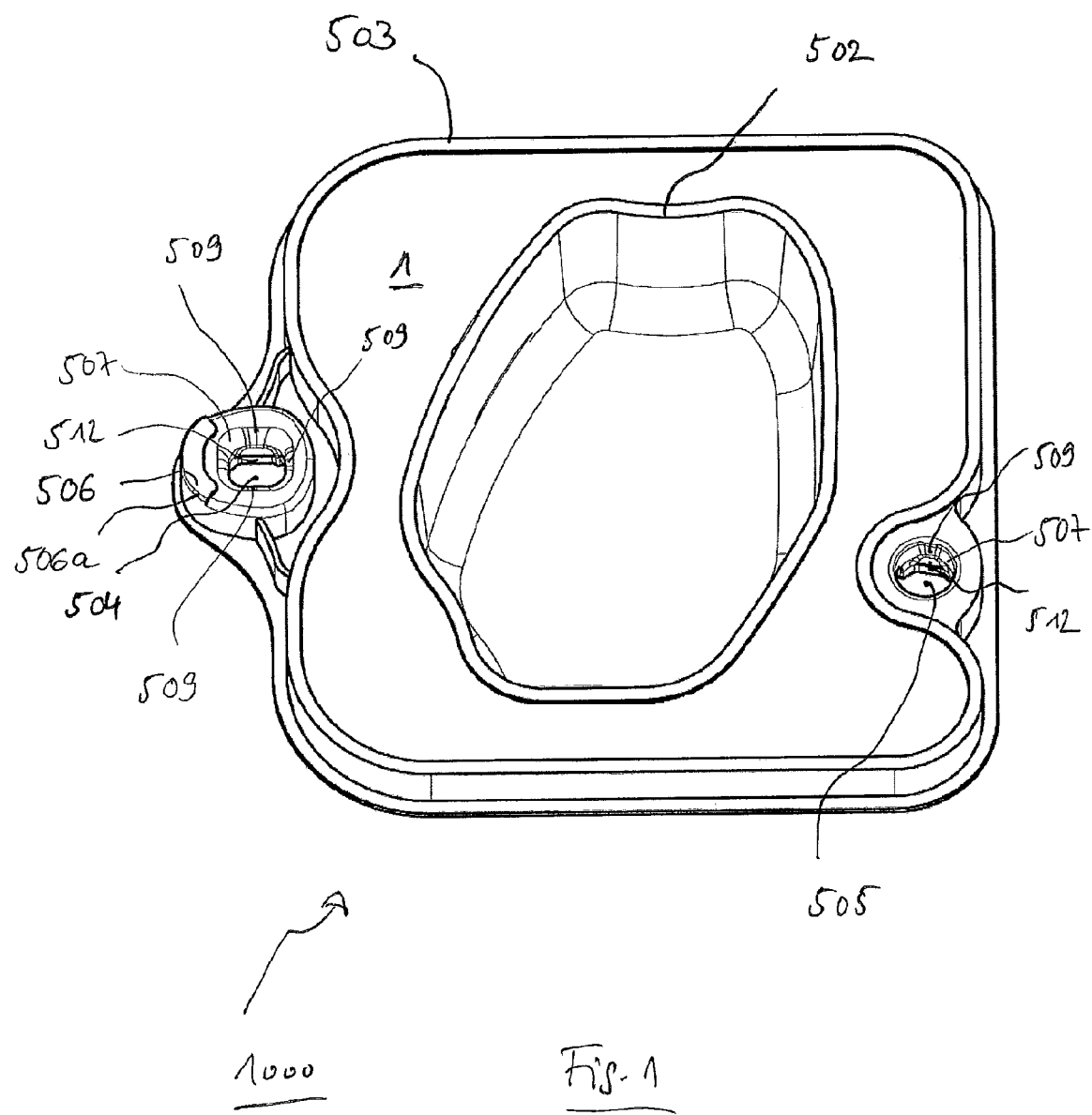
FIG. 1 shows a blood treatment cassette in a perspective top view of the side thereof which rests during use on an actuator-sensor-mat of the blood treatment apparatus.

FIG. 1 shows a blood treatment cassette 1000, also referred to herein as a cassette 1000, in a perspective plan view of the main extension plane thereof. One can see the serving side, which is referred to here as a rear side or coupling side, for the coupling of the cassette 1000 with the actuator-sensor unit 514, not shown in FIG. 1, of the blood treatment apparatus 5000, not shown in FIG. 1 either also referred to herein as machine 5000.

The blood treatment cassette 1000 comprises a hard part 1 which is optionally formed in the thermoplastic injection molding. Its modulus of elasticity range is preferably 600-2800 N/mm2. During use, the hard part 1 is, preferably, at least partially covered by a film 3, not shown in FIG. 1.

The cassette 1000 comprises in addition to elements that are relevant for the treatment of blood such as chamber boundaries 502, by way of example, at least one, preferably complete, edge bar 503. The latter serves as lifting bar when removing of the cassette 1000. In addition, the edge bar 503 serves for the sealing of portions of the cassette 1000 with respect to the machine 5000 which is not shown in FIG. 1 and the arrangement of the cassette 1000 on the machine 5000 with the aim of contributing to a flat positioning of the cassette 1000 on the machine 5000.

The cassette 1000 comprises further a first alignment device 504 which may serve, besides aligning the cassette 1000 on the machine 5000 with respect to the machine 5000, for a temporary fastening of the cassette 1000 on the machine 5000.

The first alignment device 504 may be referred to as translational, free of play origin of the arrangement of the cassette 1000. It may, as the following second alignment device 505 is also being described, be configured as an alignment latching sleeve.

The first alignment device 504 is preferably arranged at the edge or on one side of the cassette 1000. It is preferably arranged in the middle of one side or one longitudinal side, that is, centrally. Preferably, it is to be arranged with identical or comparable distance respectively to the aligning-critical structures of the cassette 1000 which are relevant to blood treatment (e.g., sensor and valve points).

A second alignment device 505 is provided as a rotationally free of play arranging alignment latching sleeve on the cassette 1000. It is preferably located on one side or on one longitudinal side of the cassette 1000 whose side is opposite to the side on which the first alignment device 504 is positioned. In this way, a large distance between the first alignment device 504 and the second alignment device 505 is achieved advantageously.

The first alignment device 504 comprises a lifting edge bar 506. It further comprises at least one insertion chamfer facing the actuator-sensor unit 514 (i.e., the insertion chamfer opens out to the actuator-sensor unit 514, for example, it opens out in a funnel-like manner) or it comprises such an insertion funnel 507.

The rounded edge of the first or second alignment device 504, 505 is thus designated in this exemplary embodiment as the insertion funnel 507. It serves a rough pre-alignment of cassette 1000.

The lifting edge bar 506 is a stiffened support surface (not a support line and not a support point, but, a surface). The lifting edge bar 506 directs the forces, resulting upon tilting the cassette when lifting it up or removing it, into the machine-sided actuator-sensor mat 515 to protect the latter from excessive wear. The lifting edge bar 506 may be spaced apart from the edge of the main extension plane in the alignment device and/or raised so that the axial force component required for the removing occurs due to the bending moment by tilting and lifting up and removing the cassette.

The lifting edge bar 506 may, as seen in FIG. 1, comprise a taper facet 506*a* which may be found on a lateral surface of the lifting edge bar 506.

The lifting edge bar 506 may further comprise, as seen in FIG. 1*b*, a rounded edge 506*b* which is positioned between the taper facet 506*a* and a mostly horizontal front area 506*c* of the lifting edge bar 506.

FIGS. 1*a* and 1*b* also show in enlarged views the lifting edge bar 506, wherein FIG. 1*a* shows an enlargement of the first alignment device 504 in the view of FIG. 1, and wherein FIG. 1*b* shows an enlargement of the lifting edge bar 506 of FIG. 1 or of FIG. 1*a*.

The first alignment device 504 and the second alignment device 505 comprise in the exemplary embodiment of FIG. 1 aligning facets 509. One can see them for the first alignment device 504 particularly well in FIG. 1*c*. Thereby, FIG. 1*c* is an enlargement of a portion of FIG. 1, which is cut for representing FIG. 1*c*, with a view from the opposite direction. FIG. 1*c* shows, due to the cut view, only three of the four aligning facets 509 of the first alignment device 504 which are distributed over the circumference of the insertion funnel 507.

The aligning facets 509 are, at least partially or in their upper area, part of the insertion funnel 507. They are in this case arranged above the latching edge 512.

It is here not seen due to the cut view that two opposite latching edges 512 are provided.

In certain embodiments, the first alignment device 504 comprises four aligning facets 509. The second alignment device 505 however, only two, as can be seen also in FIG. 1.

The aligning facets 509 may extend in a plane perpendicular to the main extension plane of the cassette 1000 (at least locally or partially).

The aligning facets 509 serve for the local or selective contact with the respective alignment pins 517, 518. Thus, they arrange or align the alignment pins 517, 518 translationally, or align them each against a translational displacement respectively.

The aligning facets 509 may, for example, border directly on the respective insertion funnel 507 or be part thereof as stated above. They extend, for example, only between about 5 and 30% of the alignment diameter 522 in the axial direction along the axis rotation of the alignment pins 517, 518 or of the alignment latching sleeves. Respectively they may extend perpendicular to the film plane or to the main extension plane prior to achieving the end of the axial overlapping with the alignment area (indicated by alignment diameter and alignment height of the alignment pins 517, 518)

The aligning facets 509 extend in the other spatial direction (i.e. parallel to the film plane or perpendicular to the symmetrical axis of the alignment pin), for example, about 10 to 80% of the alignment diameter 522.

As exemplarily shown in FIG. 1*c*, one or all aligning facets 509 may be wider at the top than at the bottom.

Aligning facets 509 or their extension axes may be arranged in planes perpendicular or substantially perpendicular to the film plane or substantially parallel to the symmetrical axis of the alignment pin.

The surfaces of the facets result in small surfaces which may be arranged substantially perpendicular to the film plane respectively. In contact with the alignment cylinder of the alignment pins 517, 518, a point or short line contact is produced per facet, in the equipping position, depending on whether the prismatic facet surface comprises a curvature perpendicular to the prism formation axis or not. To keep the tilting effect as little as possible when equipping and removing, the line of contact can be a line, for example, having a value ranging from >0 to 30% of the alignment diameter 522. This short contact line extends substantially parallel to the symmetrical axis of alignment pins 517, 518. The first alignment device 504 preferably comprises four first facet surfaces 509 (however it could also be three, five, six or more facets). The second alignment device 505 comprises in the present example, two facet surfaces 509 (exactly two, because of the advantageous intended omitting of the translational positioning along the connecting axis between the two alignment devices 504, 505).

The exactly two facet surfaces 509 in or at the second alignment device 505 are positioned parallel and mirror-inverted opposite to each other with respect to a plane which is arranged substantially perpendicular to the film plane and thereby containing the connecting line between the two alignment devices 504, 505 and both symmetrical axes of the two alignment pins 517, 518.

Two facet surfaces respectively in the first alignment device 504 are positioned in an exemplary embodiment, each parallel and mirror-inverted opposite to each other with respect to a plane which is arranged substantially at right angle or perpendicular to the film plane (hence, containing the symmetrical axis of the first alignment device 504). One sees a square alignment hole, in a top view of the film plane, essentially at the narrowest points, see FIG. 24. The square is here additionally provided again on the connecting line between the two alignment devices. The arrangement or adjustment may be in a way such that the connecting line cuts square sides at the right angle. However, the square shape and this arrangement are not necessary for fulfilling the proper function as a translational free of play zero align point. Moreover, the alignment hole-shape of a triangle, pentagon or hexagon with any rotational arrangement is also possible, and it is being encompassed by the present invention.

The alignment facets 509 may be part of the insertion funnel 507. They are, at least in part, advantageously disposed on an upper area of the insertion funnel 507, see also the enlarged view in FIG. 1*c*.

In FIG. 1*c*, the side of the cassette 1000 which faces, during use, to the actuator-sensor mat 516, is disposed on top. The side of the cassette 1000 or that side of the cassette 1000 which faces, during use, at the machine door is disposed below.

As can be seen in FIG. 1*c*, the aligning facets 509 in certain exemplary embodiments are disposed above the latching edge(s) 512. Above, is to be understood here as to be closer to the actuator-sensor mat 516; below is to be understood as closer to the front of the cassette or the machine door.

The latching edges 512 may be straight or curved edges, in some embodiments. This design nearly allows a point contact with a latching diameter 521 of one of the alignment pins 517, 518 not shown in FIG. 1, as opposed to an elongated or large surface contact.

As the first alignment device 504 and/or the second alignment device 505 are, in certain exemplary embodiments, not only responsible for aligning but also for latching the cassette 1000 to the machine 5000 or contribute to this, they may therefore also be referred to in such embodiments as alignment latching devices.

Figure 2:
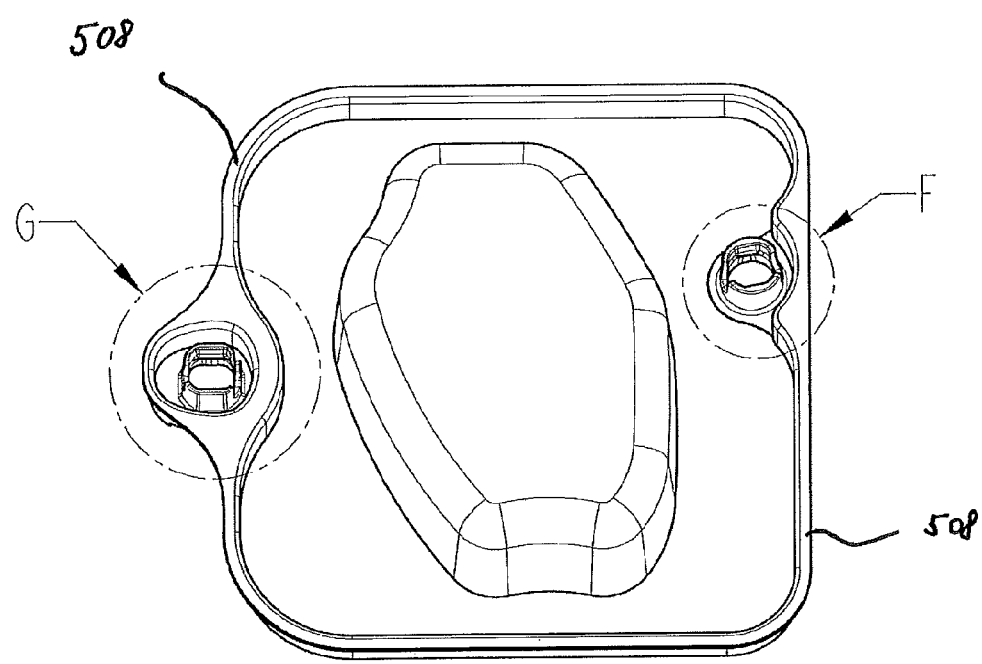
FIG. 2 shows the blood treatment cassette of FIG. 1 in a perspective view of the door side, i.e. to the side opposite to that shown in FIG. 1, which rests during use on a machine door of the blood treatment apparatus.

FIG. 2 shows the cassette 1000 of FIG. 1 in a perspective plan view on the door side. The door side serves for the optional pressing by a machine door 524, not shown in FIG. 2. It is located opposite of the coupling side and may be referred to as the front side.

FIG. 2 shows a further, again only optionally shown here, complete edge bar 508. It may be referred to as multi-functional since it does not only serve as a surface (preferably in a plane) for the transfer of the pressing effect by the machine door 524, but also for the stiffening of the cassette 1000 and the stiffened connection of the first alignment device 504 and/or the second alignment device 505. It may also serve for the transfer of the forces of equipping and removing and the force paths from (any) of those points at which the user touches the cassette 1000 in order to remove it and from which the emerging forces may be introduced into the cassette 1000 and the alignment pins 517, 518, through the first alignment device 504 and/or the second alignment device 505.

Figure 3:
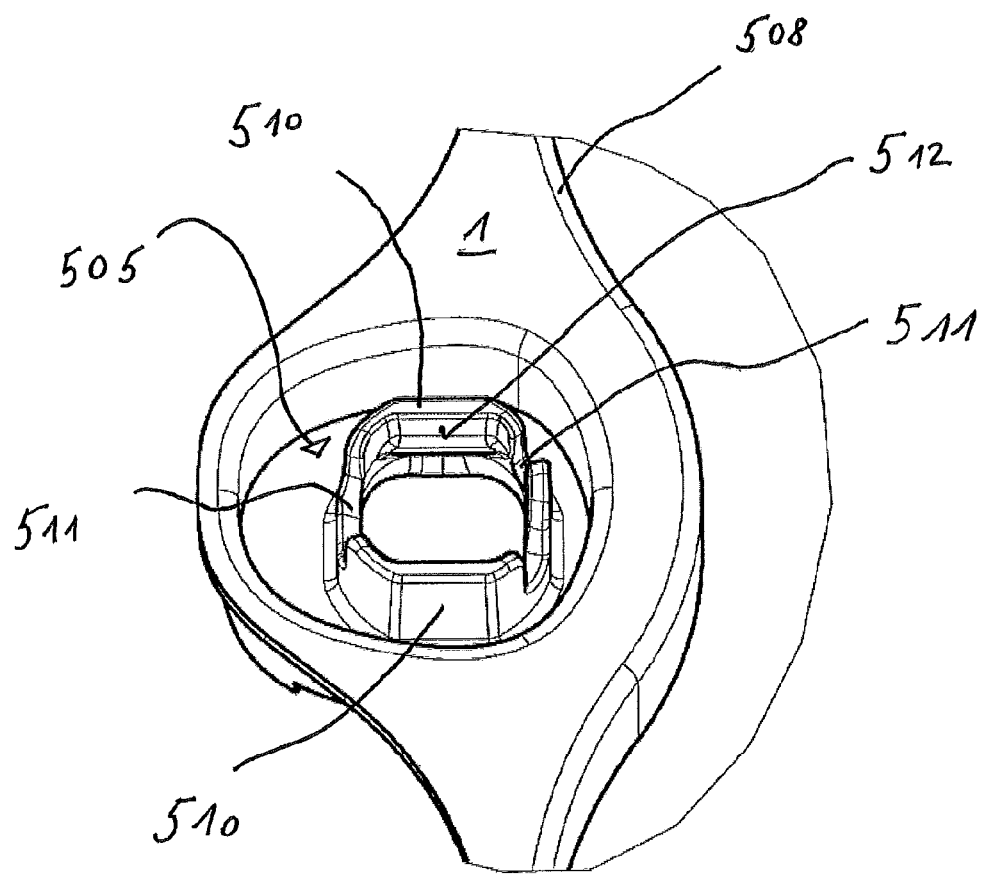
FIG. 3 shows the detailed view G of FIG. 2.

FIG. 3 shows the detailed view G of FIG. 2.

Figure 4:
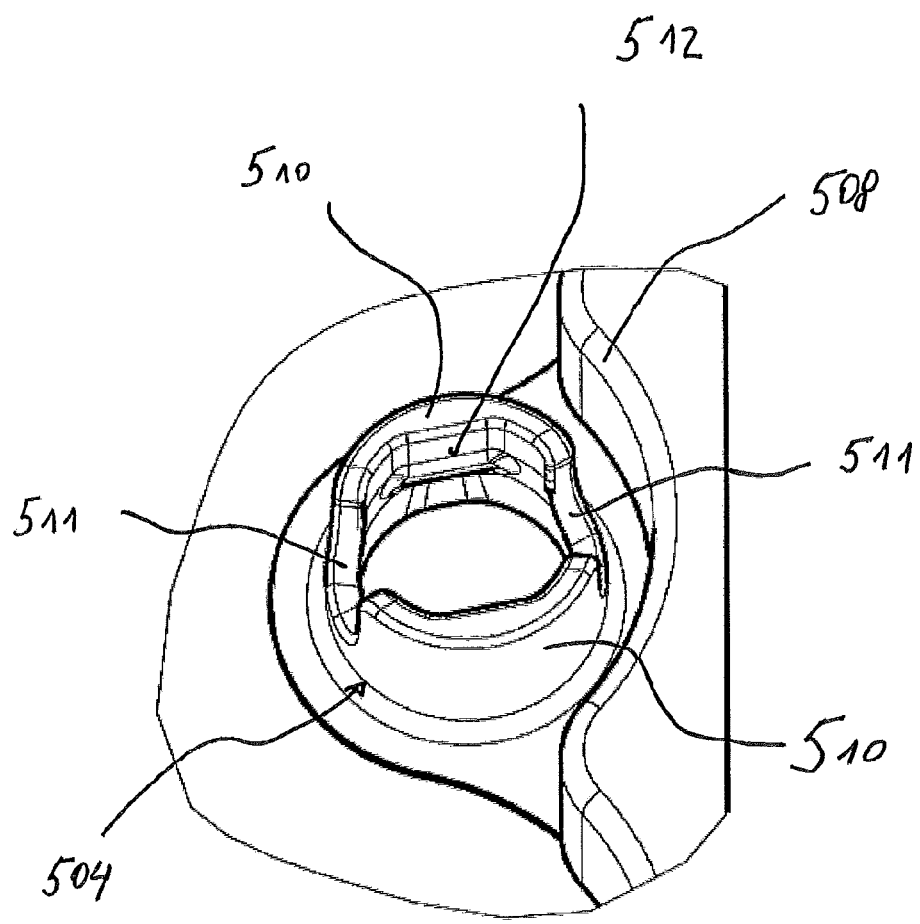
FIG. 4 shows the detailed view F of FIG. 2.

FIG. 4 shows the detailed view F of FIG. 2.

Snap-in pins which are parts of the first alignment device 504 and/or second alignment device 505, are designated in the figures by the reference numeral 510. For each alignment device 504, 505 at least two snap-in tongues 510 are preferably provided, preferably disposed opposite to each other.

The snap-in tongues 510 may be adapted to be elastically bendable for the intended use. They may be separated from each other by cuts 511, which contributes to the specific bending flexibility of the snap-in tongues 510.

Each snap-in tongue 510 comprises at least or exactly one latching edge 512. The latter extends in a first plane parallel to the main extension plane, preferably locally, in particular, in a plane parallel to the main extension plane of the cassette 1000 to allow a shifting ability relative to the alignment pins 517, 518 without changing the retention force of the latching, and further to ensure a priority of alignment force of the aligning facets to 509.

In a preferred embodiment, in a second plane which is perpendicular to the main extension plane, the latching edge 512 is a curved edge or comprises such one. This form allows a line of contact, with the similarly curved grooves of the alignment pins 517, 518 and thus acting on friction minimization in equipping and removing procedures.

Figure 5:
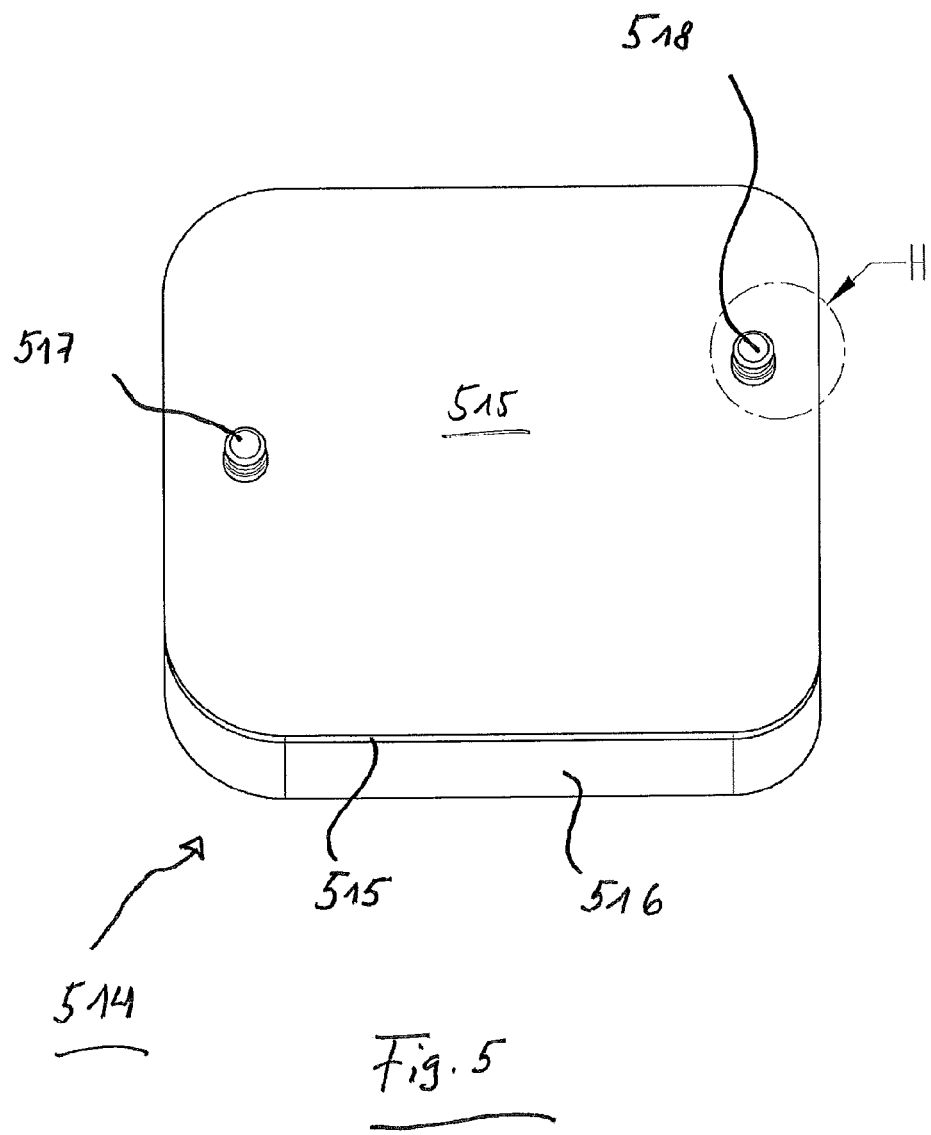
FIG. 5 shows the actuator-sensor unit of the blood treatment apparatus according to the present invention in a perspective top view of the main extension plane of the actuator-sensor unit.

FIG. 5 shows the actuator sensor unit 514 of the machine 5000 in a perspective plane view on the main extension plane.

Figure 6:
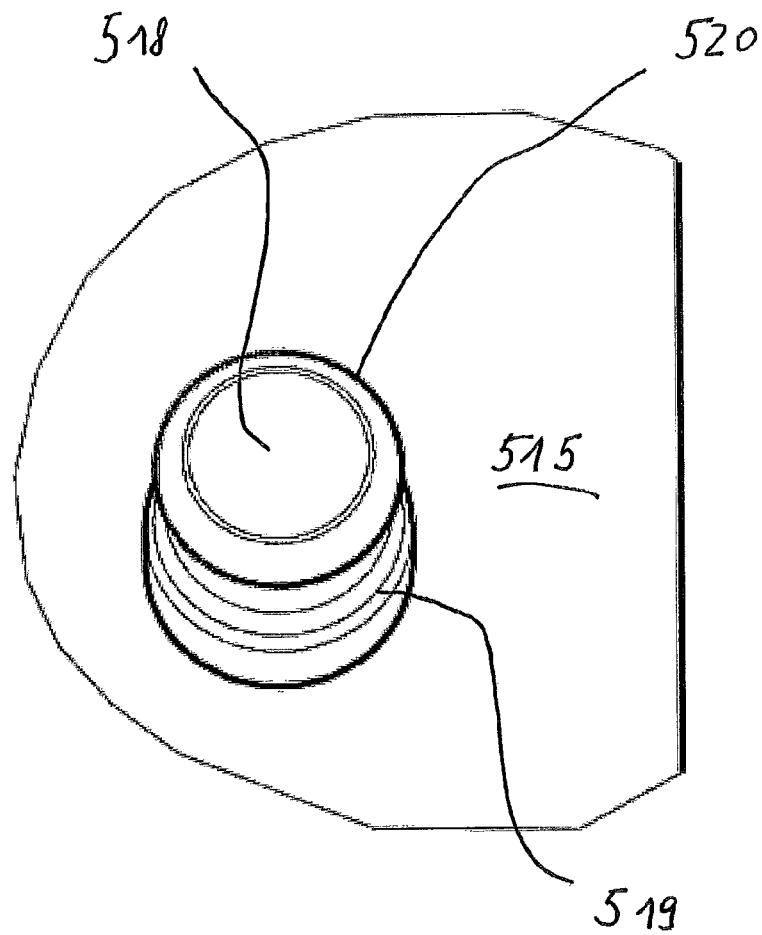
FIG. 6 shows the detailed view H from FIG. 5 in a perspective view.

FIG. 6 is the detailed view H from FIG. 5 in perspective.

Figure 7:
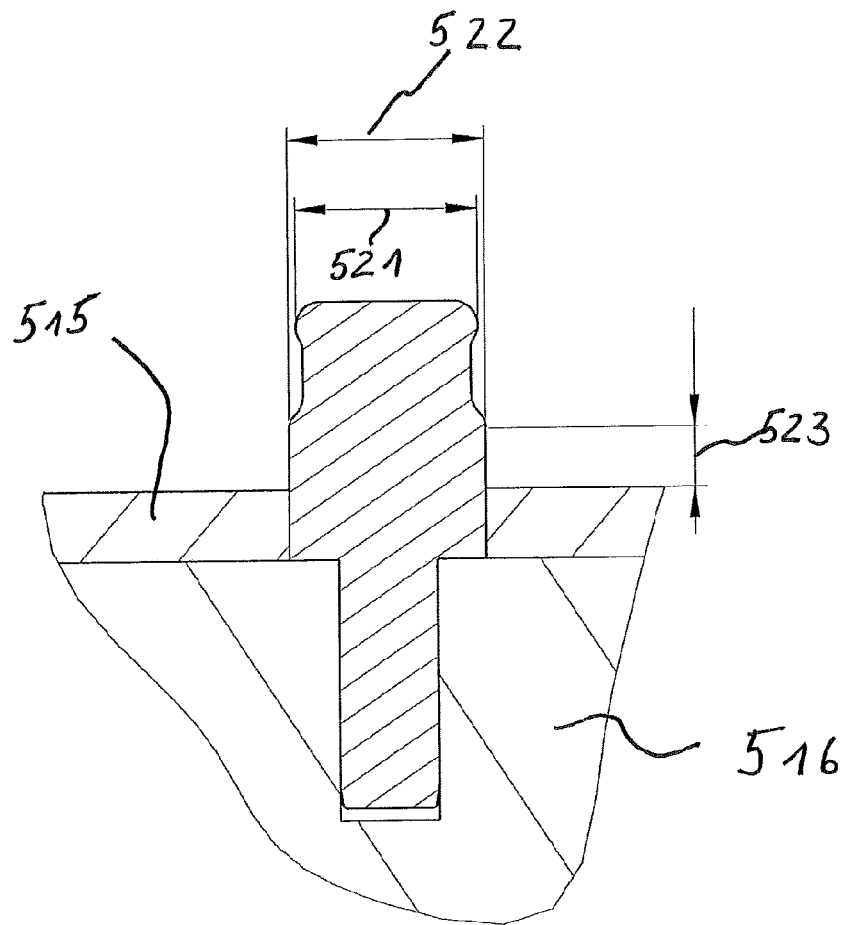
FIG. 7 shows the detailed view H from FIG. 5 in a sectional view.

FIG. 7 is the detailed view H from FIG. 5 in section.

In the figures, reference numeral 514 refers to the actuator-sensor unit 514 of the machine 5000, wherein 515 designates the actuator-sensor mat of the unit 514. The actuator-sensor mat 515 is only optionally provided and configured also in a planar manner for the preferred planar coupling on the cassette 1000.

516 designates the actuator-sensor plate. It is a more rigid reference body and base material for the first and second alignment pins 517 or 518.

The first alignment pin 517 is provided for latching with the first alignment device 504, while the second alignment pin 518 is provided for latching with the second alignment device 505.

In certain exemplary embodiments, the first and/or the second alignment pins 517 or 518 may comprise the following characteristics which may be provided independent from each other:

They may be embodied as rotationally symmetrical parts which are cost-effective, accurate and convenient to assemble.

They may be made of stiff, abrasion-resistant material (such as ceramic, steel, etc.).

They may be provided with a polished surface (friction-minimization, cleanability, tilt-reduction).

They may be adapted to be identical elements (cost-effective, no interchangability risk).

They may have, as exemplarily shown in FIG. 6, rounded transitions 519 and preferably strong, rounded front-area edges 520 for the minimization of friction by straight or canted or tilted relative movements against the first and second alignment device 504, 505 and for the optimization of the threading into the alignment devices 504, 505.

They may comprise a latching diameter 521 which is less or smaller than its alignment diameter 522. This optimizes the threading and reduces the risk of tilting in equipping and removing.

They may have an alignment height 523, which is in the range of 0.1 to 0.5 times of the alignment diameter 522. This advantageously serves to limit the maximum, tilt-enabled tilt angle during equipping and removing.

The limitation of the tilting advantageously takes place in some embodiments according to the present invention in that the tilting angle steadily increases during the tilting removal movement. Due to the concurrent lifting, the alignment device is moved relative to the alignment pin parallel with the increase of the tilting angle. Since the alignment height 523 of the alignment pins 517, 518 is limited, the corresponding alignment device 504, 505 becomes disengaged from the alignment diameter 522 of the alignment pin 517, 518, already in a non-critical range with respect to the tilt range with a low tilt angle in the range of the alignment facts 509.

Figure 8:
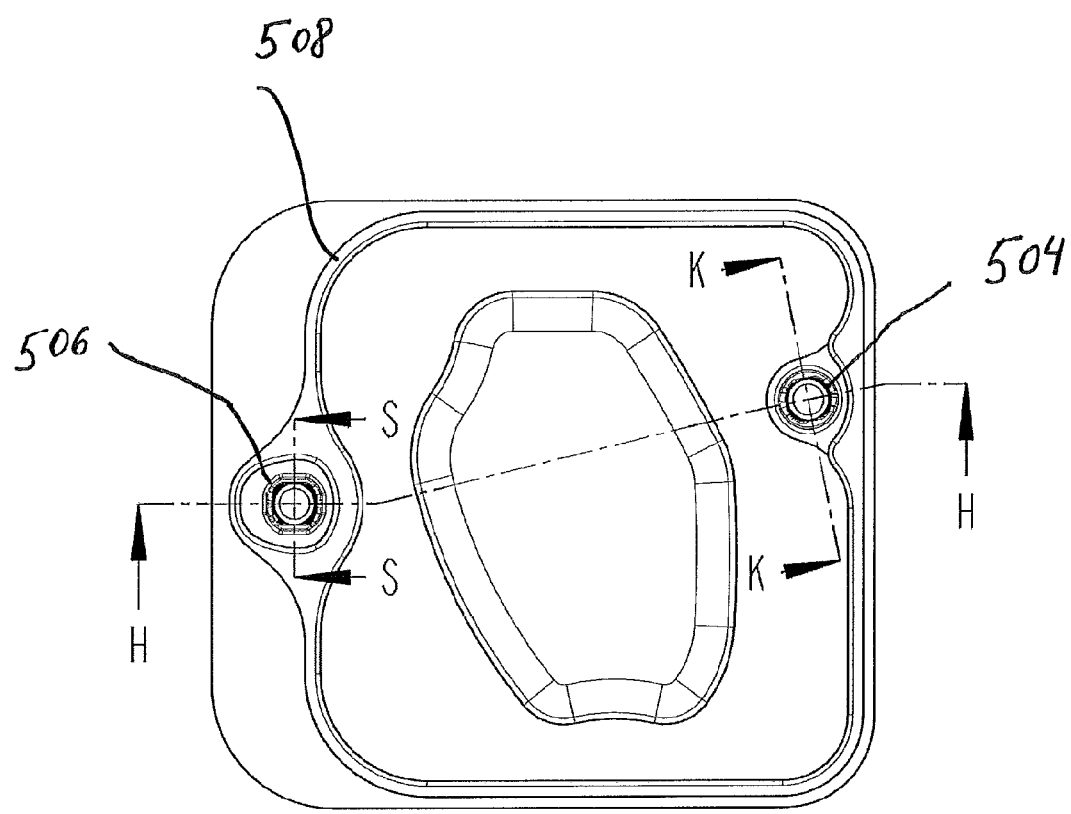
FIG. 8 shows in a top view the blood treatment cassette and sections of the blood treatment apparatus in an activated state without a purely optional machine door.

FIG. 8 shows a plan view of the cassette and sections of the machine in the state of equipping without a purely optional machine door.

Figure 9:
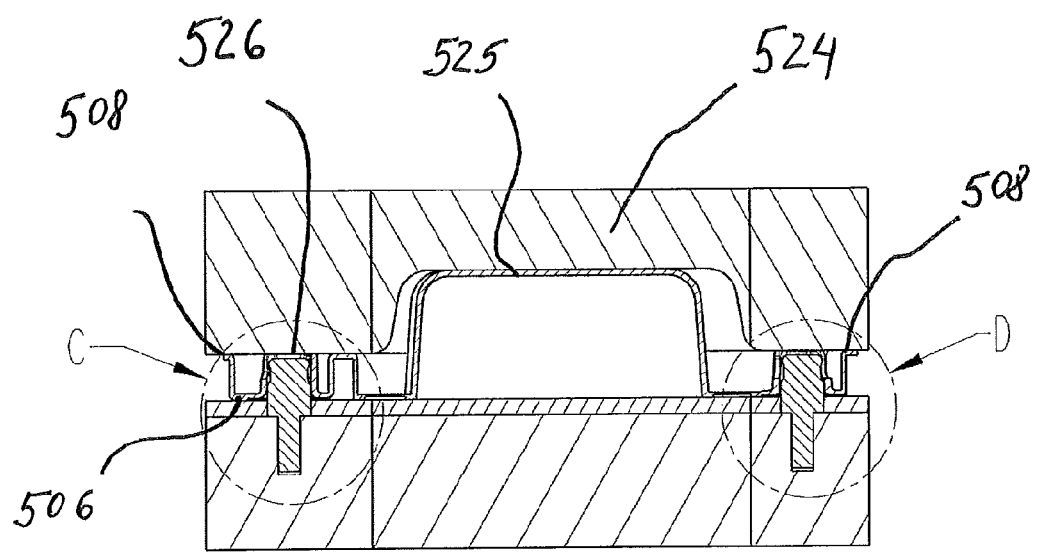
FIG. 9 shows a section or cut along the line H-H of FIG. 8; the optional machine door of the blood treatment apparatus is added to the disclosure of FIG. 8.

FIG. 9 shows a section along the line H-H of FIG. 8; the optional machine door 524 is supplemented relative to FIG. 8; the pressed state is shown.

The optional machine door 524 serves for the pressing of the cassette 1000 as well as its disposition in a plane in case the cassette 1000 should, at one point, have been placed in twisted or bent-through. This arrangement is performed at the actuator-sensor unit 514 by the complete edge bar 508 and possibly further, optional, planar support zones 525 and 526.

The cassette 1000 is placed during the blood treatment using a friction closure on the actuator-sensor mat 515. This ensures that the aligning position of the cassette 1000 is maintained even when mechanical or fluidic forces strike the cassette 1000 or the associated connection hoses.

In certain exemplary embodiments, in the pressed state, all support surfaces of the machine door 524 that come in touch with the cassette 1000 are disposed parallel to the main plane of the cassette 1000. This advantageously ensures a sole aligning of the cassette 1000 through the alignment pins 517 and 518.

Figure 10:
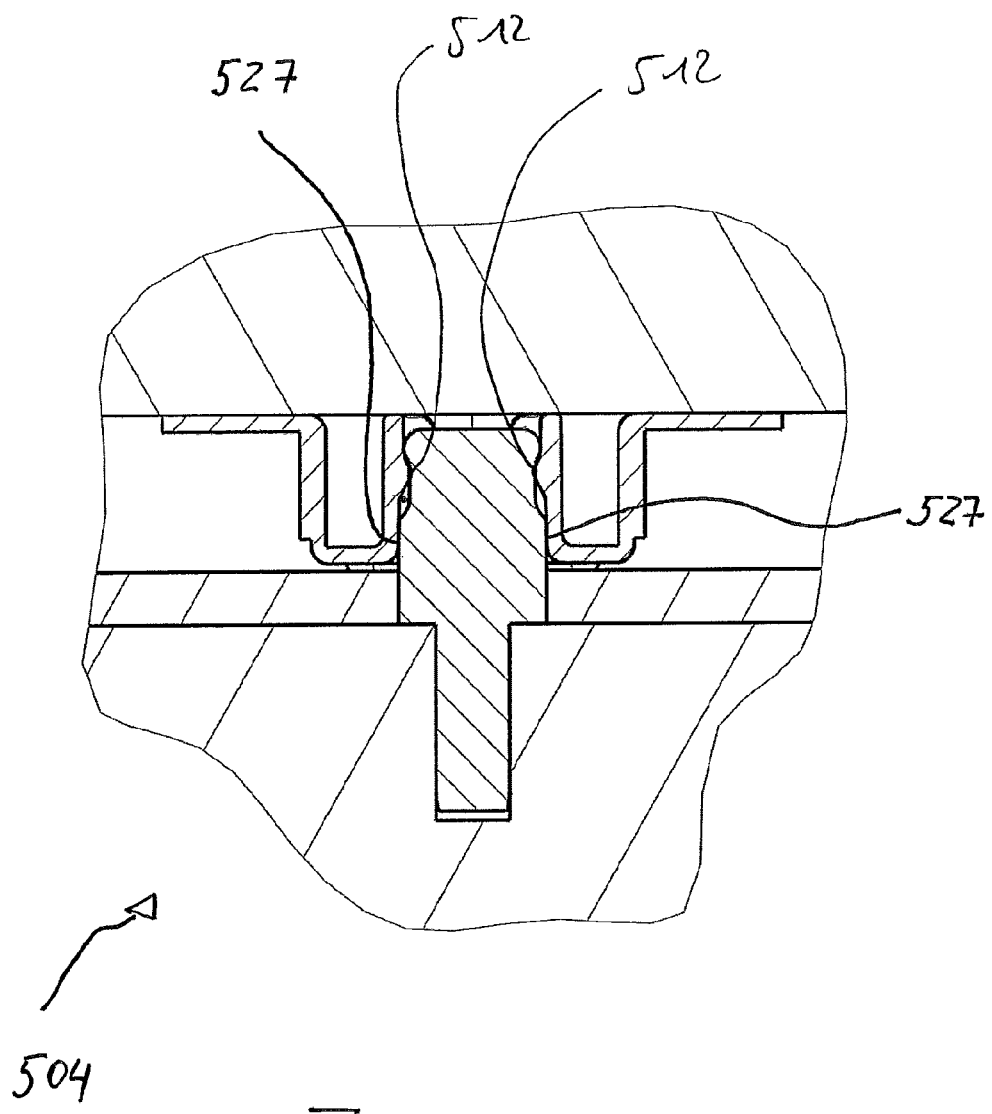
FIG. 10 shows a first alignment device of the blood treatment cassette in detail, along the line S-S of FIG. 8 in a sectional view.

FIG. 10 shows the first alignment device 504 in detail, along the line S-S of FIG. 8 in a sectional view.

Figure 11:
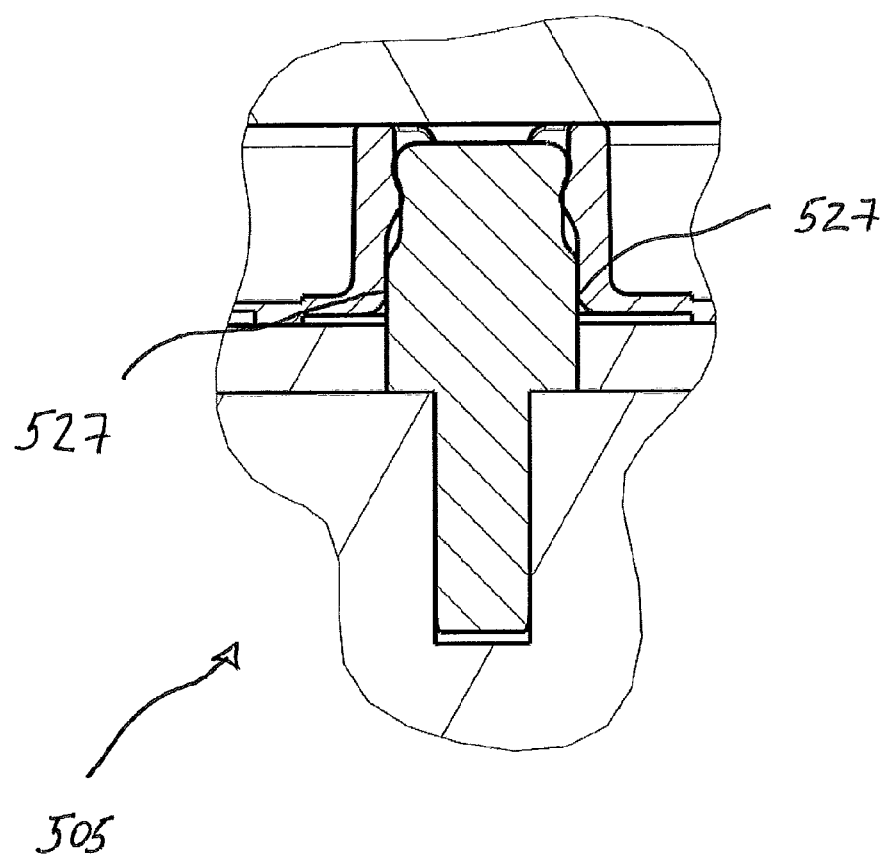
FIG. 11 shows a second alignment device of the blood treatment cassette in detail, along the line K-K of FIG. 8 in a sectional view.

FIG. 11 shows the second alignment device 505 in detail, along the line K-K of FIG. 8 in a sectional view.

Figure 12:
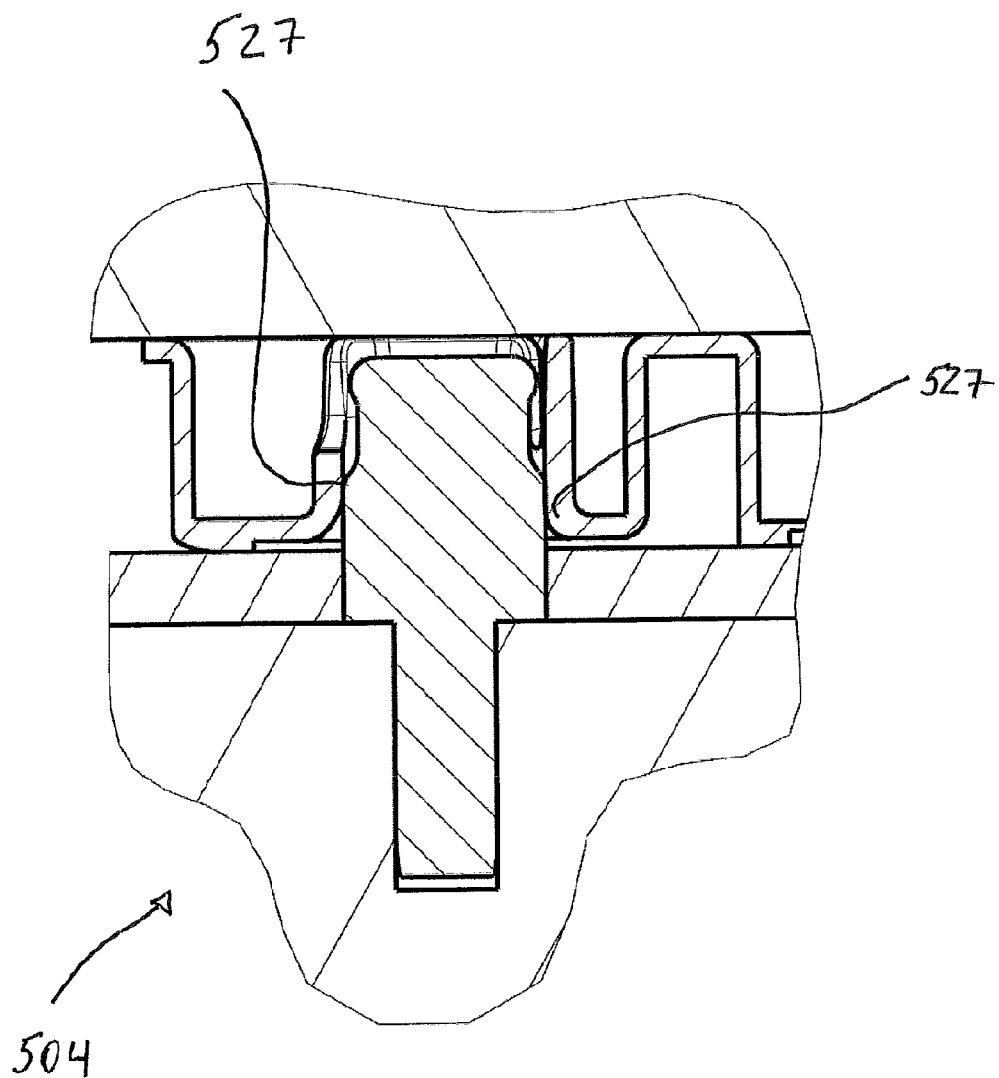
FIG. 12 shows a detailed view of the first alignment device along the line H-H of FIG. 8 in a sectional view.
Figure 13:
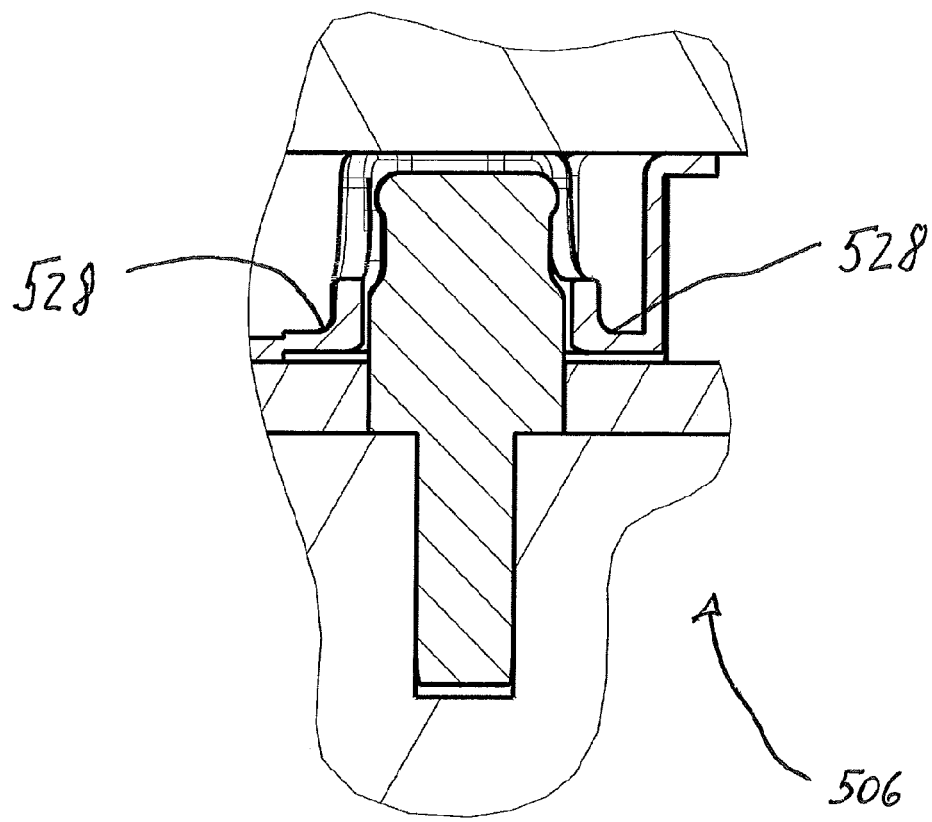
FIG. 13 shows a detailed view of the second alignment device along the line H-H of FIG. 8 in a sectional view.

FIG. 12 and FIG. 13 show detailed views of the first and second alignment device 504 and 505 along the line H-H of FIG. 8 in a sectional view.

In each of the FIGS. 10-12, the first and the second alignment device 504, 505 are latched by the alignment pins 517 and 518.

FIG. 10 shows the first alignment device 504 in a cutting direction S-S from FIG. 8, in which the two short opposite contact lines or contact line sections 527 have each the same length and have a similar length in comparison (because the lifting-edge distance to the cassette edge bars on top and bottom is very long).

FIG. 11 shows an analog section to the section of FIG. 10. What has been said with regard to FIG. 10 may apply to FIG. 11 as well.

FIG. 12 shows the section through the first alignment device along the cut H-H, which is, in particular, unfavorably effected by the introduction of larger tilting during equipping and removing, as represented in FIGS. 20 to 23. In FIG. 12, one looks upon a left, shorter line contact portion 527 on the left, which is located further away from the actuator-sensor mat 515 through the inverted and anticipated pre-tilted arrangement of the alignment narrow point according to FIG. 26 than the longer right line contact portion 527 on the right.

Figure 24:
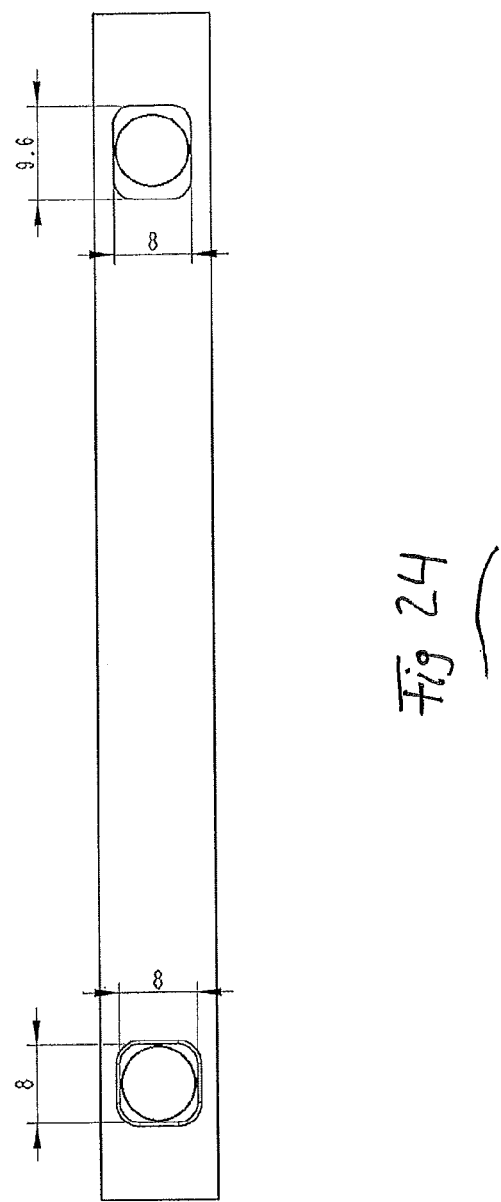
FIG. 24 shows in a schematic view, the first and second alignment device with merely exemplary dimensioning.

In FIGS. 10 to 12, the line contact portions 527 or line segments touch the alignment pins 517,518 preferably in punctiform at the alignment diameter, see also FIG. 24.

The tolerance situation of the passage width between the line contact portions 527 and the alignment diameters 522 of the alignment pins 517, 518 is preferably selected such that always a play-free or zero backlash (i.e. no play) is given, to be specific, beginning at the play-free arrangement till the completed alignment latching of the cassette 1000. This is due to the punctiform or short-lined arrangement of all (in this case four) aligning facets 509 of the first alignment device and the (here: two) aligning facets 509 of the second alignment device 509. If the comparatively harder alignment pin 517, 518 is pressed with the comparatively softer aligning facets 509, wherein the diameter of the alignment pins 517, 518 as measured by the distance between opposite aligning facets preferably comprises an excess, the softer surface deforms at least partially elastic and partially plastic. Due to this deformation, the point-contact becomes a circular or oval-shaped contact surface and a line-contact becomes a surface-contact. The free of play in the latched state remains on the one hand side always guaranteed. The pressing forces and thus the frictional forces during removal remain on the other hand sufficiently low due to the low modulus of thermoplastics (such as 1800 N/mm2) and also due to the partially plastic deformation, so that no material breaking is caused during tilting.

The plastic part of the expansion expands further in the course of the treatment, so that the removal is facilitated. Moreover, by the machine door 524, which grants friction closure, a displacement of the cassette 1000 during treatment is securely prevented.

Rounded transitions or splits 528 of the second alignment device 505 on which prevails play, prevent an alignment in their direction.

The longitudinal axis of the second alignment device 505 is oriented towards the center of the through-hole or -opening of the first alignment device 504 in order to limit, to a maximum, the possibility of rotation of the cassette 1000. At the same time, the longitudinal axis points approximately in the direction of the shortest distance to the edge bar 508 of the cassette 1000.

The cuts or slits 511 between the snap-in tongues 510 are also preferably arranged symmetrically to the connecting axis or line between the first and the second alignment device 504, 505 and serve to increase the tilt-movement freedom.

Figure 14:
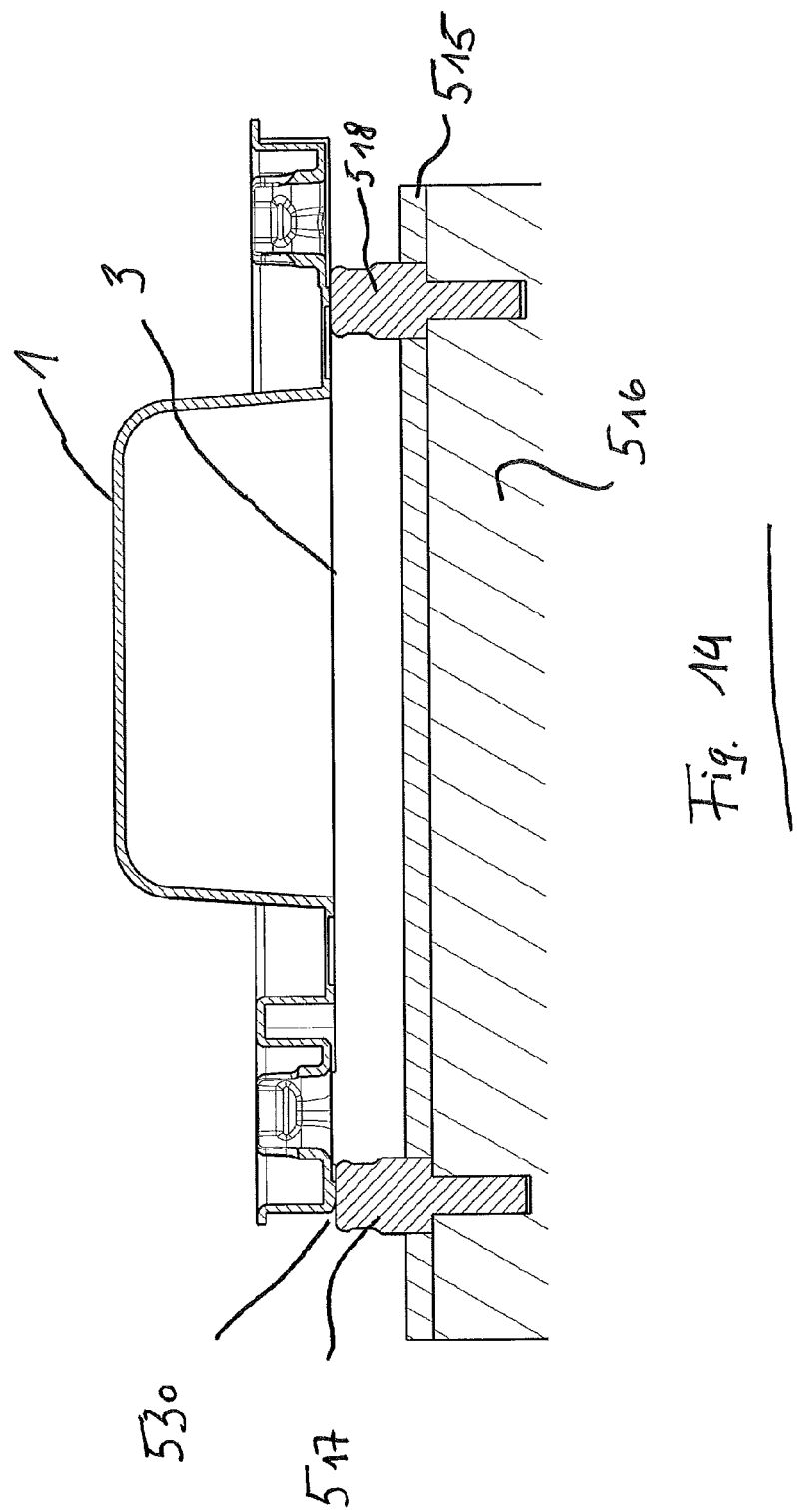
FIG. 14 shows a first step of the equipping process, the placing of the cassette.

FIG. 14 shows a first step of the equipping procedure, the positioning of the cassette 1000. The reference numeral 3 designates the film.

Figure 15:
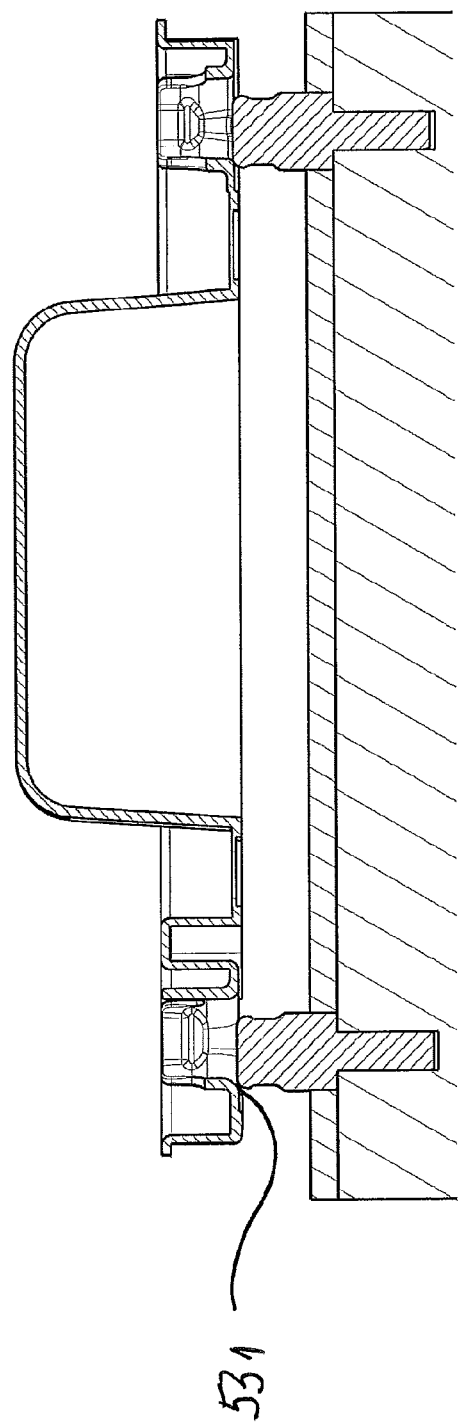
FIG. 15 shows the second step of the equipping process, the beginning of threading.

FIG. 15 shows the second step of the equipping procedure, the beginning of the threading.

Figure 16:
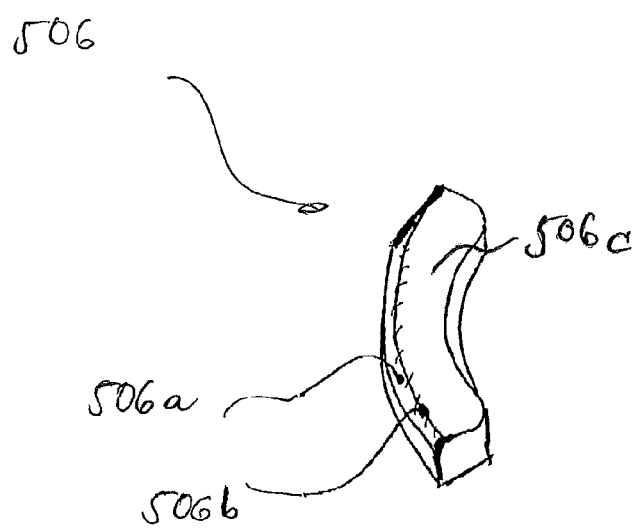
FIG. 16 shows the third step of the equipping process, the one-sided termination of threading.

FIG. 16 shows the third step of the equipping procedure, the one-sided completion of the threading on one side.

FIG. 17 shows the fourth step of the equipping procedure, the completion of the threading on both sides.

FIG. 18 shows the fifth step of the equipping procedure, the completion of an alignment latching on one side.

Figure 19:
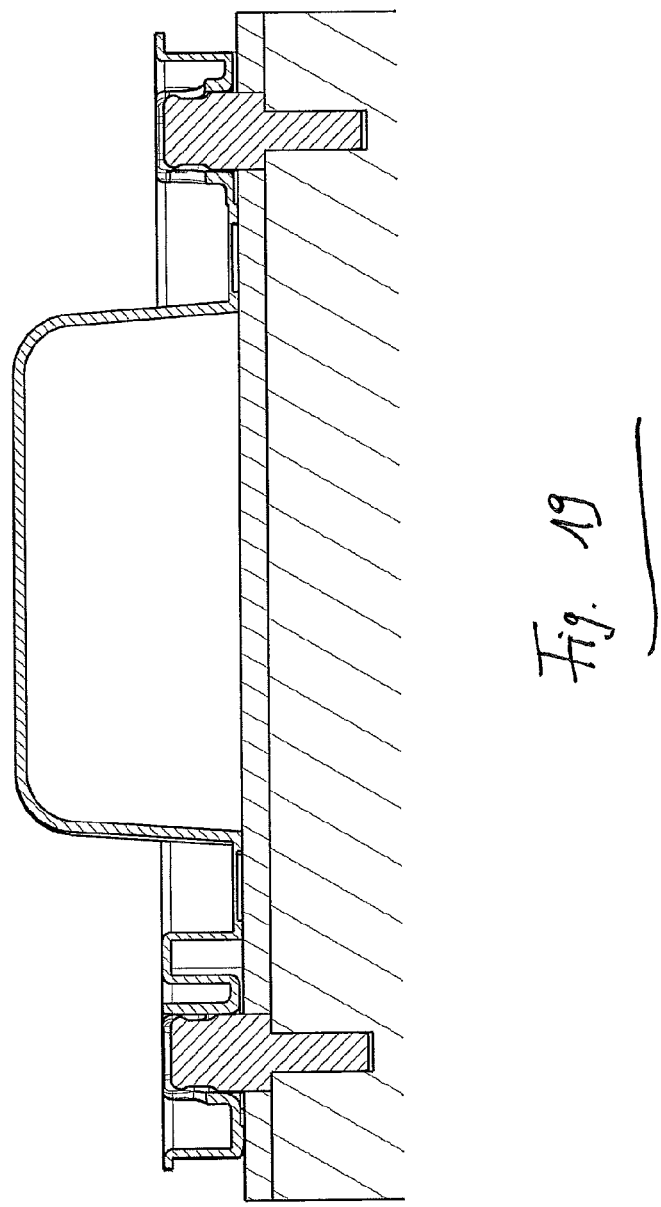
FIG. 19 shows the sixth step of the equipping process, the double-sided termination of the alignment latching.

FIG. 19 shows the sixth step of equipping procedure, the completion of the alignment latching on both sides.

In the equipping procedure represented in the previous figures which are in the following further explained, the flat front areas of the alignment pins 517, 518 allow in connection with the flat and flat front area of the cassette 1000 correspondingly generously measured an ergonomically favorable, allowable lateral misalignment 530 around both alignment devices 504, 505 of preferably 0.5-2.5 times of the alignment diameter 522 in the manual placement of the cassette 1000 without risk of damage.

At the beginning of the threading, the lateral misalignment 531 is, due to the corresponding insertion chamfers 507, preferably within the 0.1-to 0.2 times of the alignment diameter 522; this is ergonomically favorable since the operator may observe the threading long before reaching the centricity through the rapidly commencing approach movement at the edges of the chamfers in the Z direction and the further threading process is then guided by the chamfers 507.

After completion of the threading on one side, one of the alignment devices 504, 505 is threaded to the extent that its latching edges 512 abut the rounded front-area edge 520 of an alignment pin 517, 518, while the other alignment device 504, 505 has not yet begun its threading or has not yet completed it. Due to the selected distances between the alignment devices 504, 505 in connection with the height difference between the total height of an alignment pin 517, 518 and the alignment height 523, a maximum angle tilting 532 between the main extension plane of the cassette 1000 and the main extension plane of the machine 5000 is about 1-3°. In connection with the geometric designs, 'rounded front side of the alignment pins', snap-in diameter 'less than alignment diameter' and 'insertion chamfers of the alignment devices', tilting and thus movement disabilities or material overloads are prevented during any executed threading At the beginning of latching, both alignment devices 504, 505 are so far inserted into the alignment pins 517, 518 that a distance 533 of the two main extension planes (of cassette 1000 on the one hand and the actuator-sensor mat 515 on the other) is more (only) than approximately 0.02-0.04 times of the distance of the alignment points. Through any order and angular position of the subsequent latching, a tilting angle 534 of more than approximately 1.5 degrees may not be reached.

This low tilting angle 534 caused in connection with the material and geometry selection does not cause any tilting force which leads to the overstress of the material of the cassette 1000. These tilting forces signify at the same time no exceeding of the maximum targeted snap-in force of about 50 N in all tolerance positions of the measurements.

Figure 20:
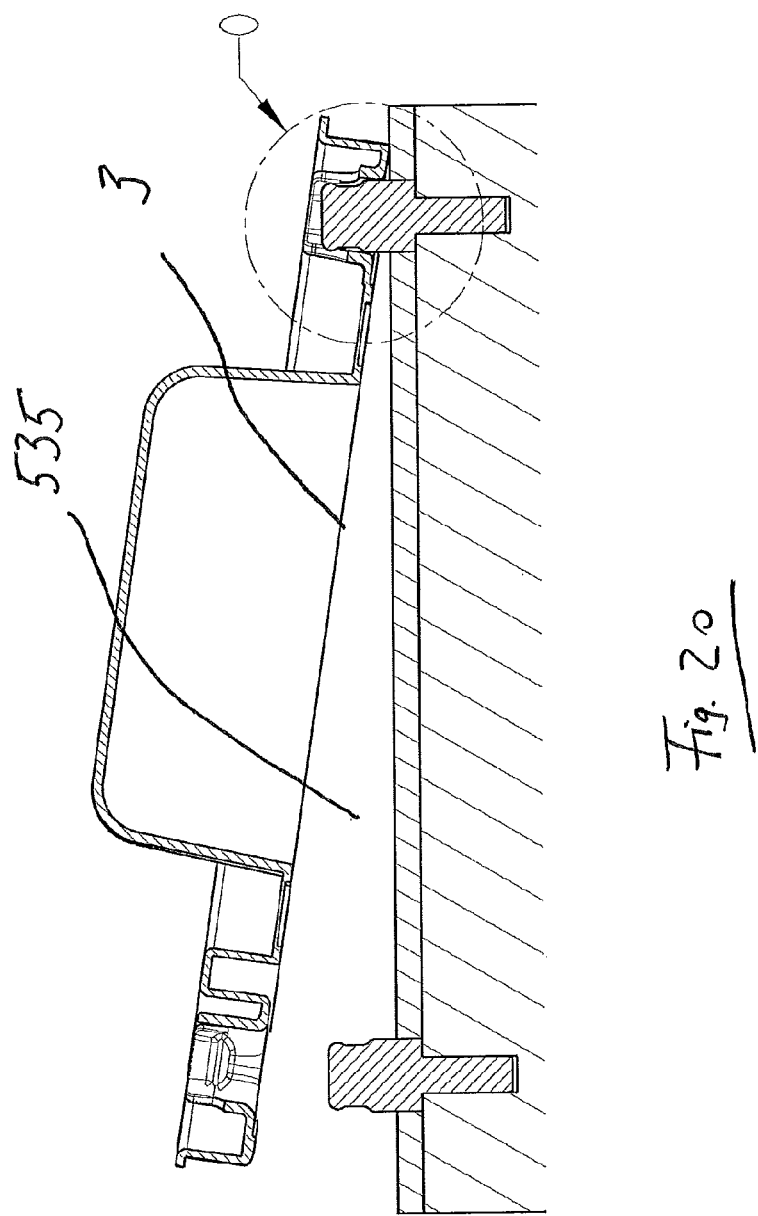
FIG. 20 shows a critical moment of the unlatching at the second alignment device during the removing process.

FIG. 20 shows a critical moment of the unlatching or snap-off at the second alignment device 505 during the removal process.

Figure 21:
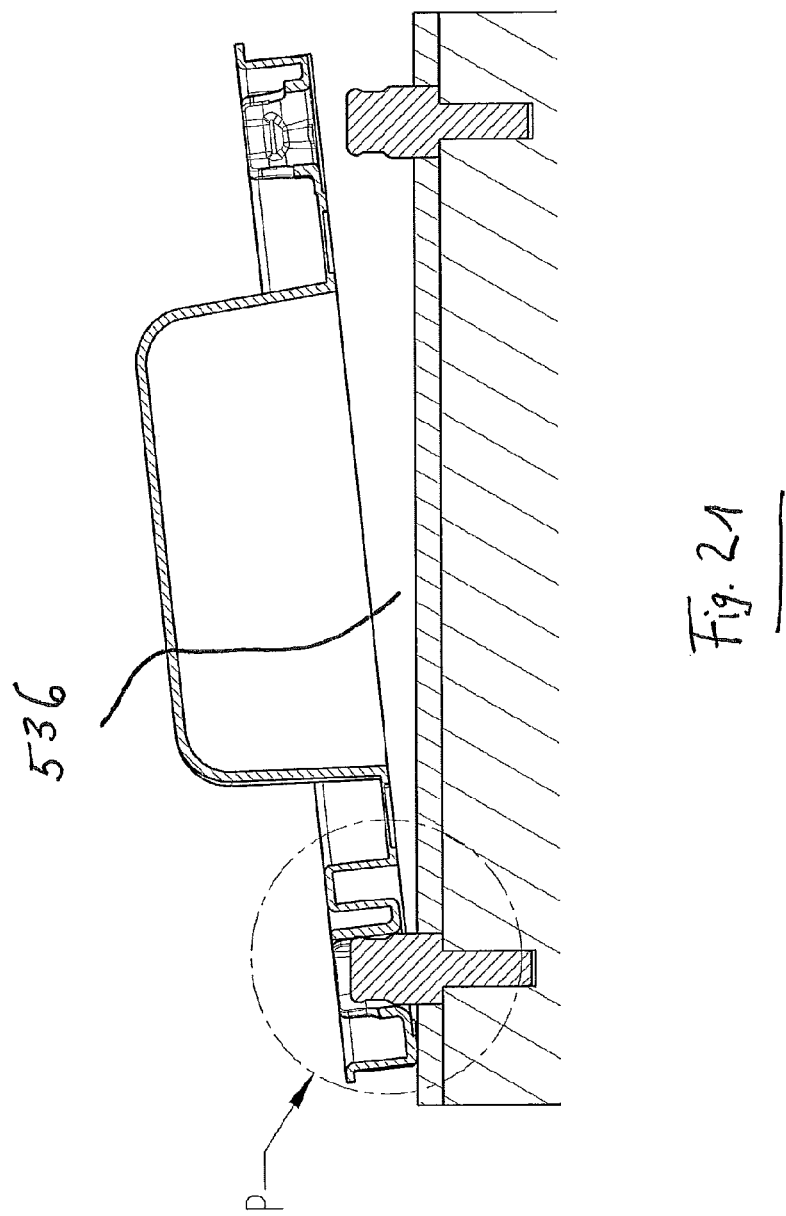
FIG. 21 shows a critical moment of the unlatching at the first alignment device during the removing process.

FIG. 21 shows a critical moment of the unlatching at the first alignment device 504 during the removal process.

Figure 22:
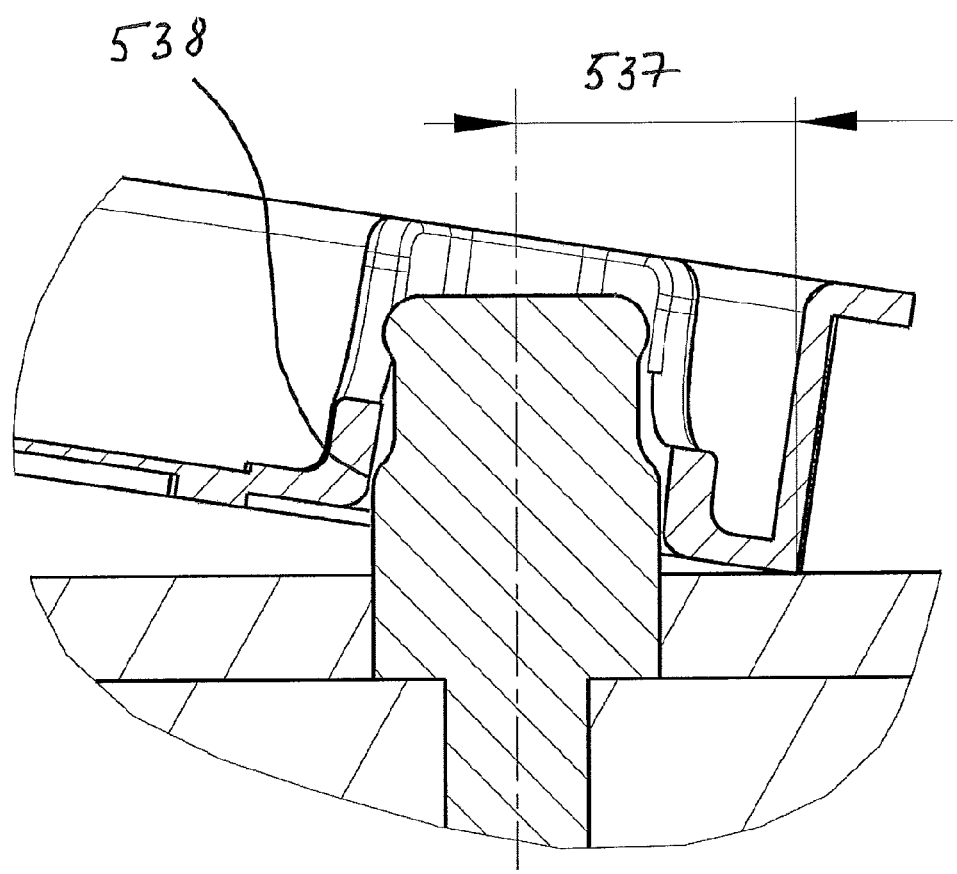
FIG. 22 shows the section O of FIG. 20 in detail.

FIG. 22 shows in detail the section O of FIG. 20.

Figure 23:
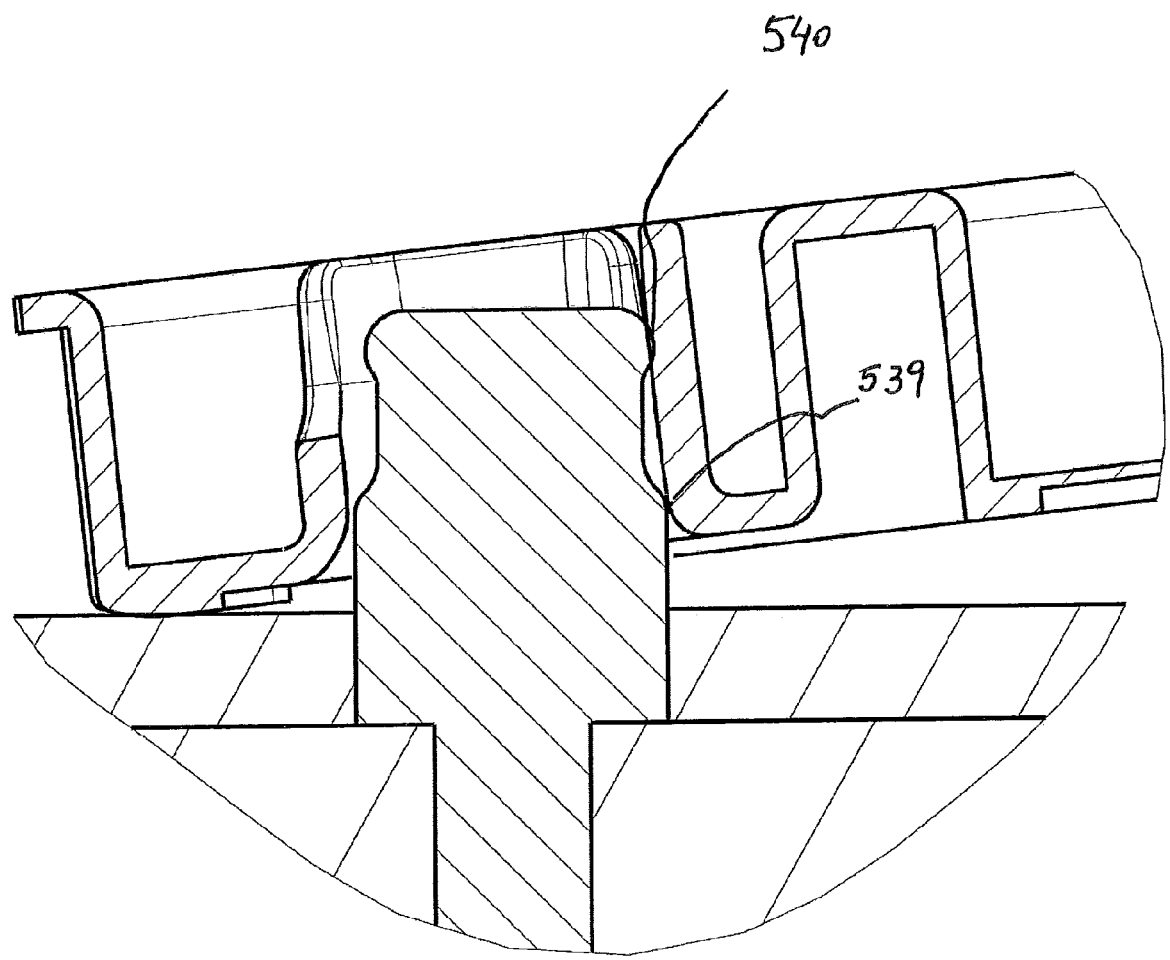
FIG. 23 shows the section P of FIG. 21 in detail.

FIG. 23 shows in detail the section P of FIG. 21.

In the removing process represented in the preceding figures and further explained in the following, the unlatching takes place in an angular range 535, 536 up to approximately a maximum of 10°, based on the selected measurements of the two alignment devices 504, 505. The worst removal process, by which this tilt angle at the moment of the unlatching may be achieved, is shown in FIG. 20 and FIG. 21.

At the alignment device 505, the slot-like through-hole or opening, in connection with the cuts 511 between the snap-in tongues 510 and in connection with a lifting edge distance 537 and the heights and diameter ratios, prevents the tilting situation 538 from being reached.

At the first alignment device 504, the tilted arrangement 541 of the alignment through-hole, in connection with the cuts 511 between the snap-in tongues 510 and in connection with the lifting edge distance 537 and the height and diameter ratios, prevents the tilting situation 539 from being reached. An optionally provided tongue 540, flatly embodied, may not cause a critical tilting, since it is bendable just like the snap-in tongues 510.

FIG. 24 shows in a schematic view, the first and second alignment devices 504, 505 with merely exemplary dimensioning and the herein received alignment pins.

Figure 25:
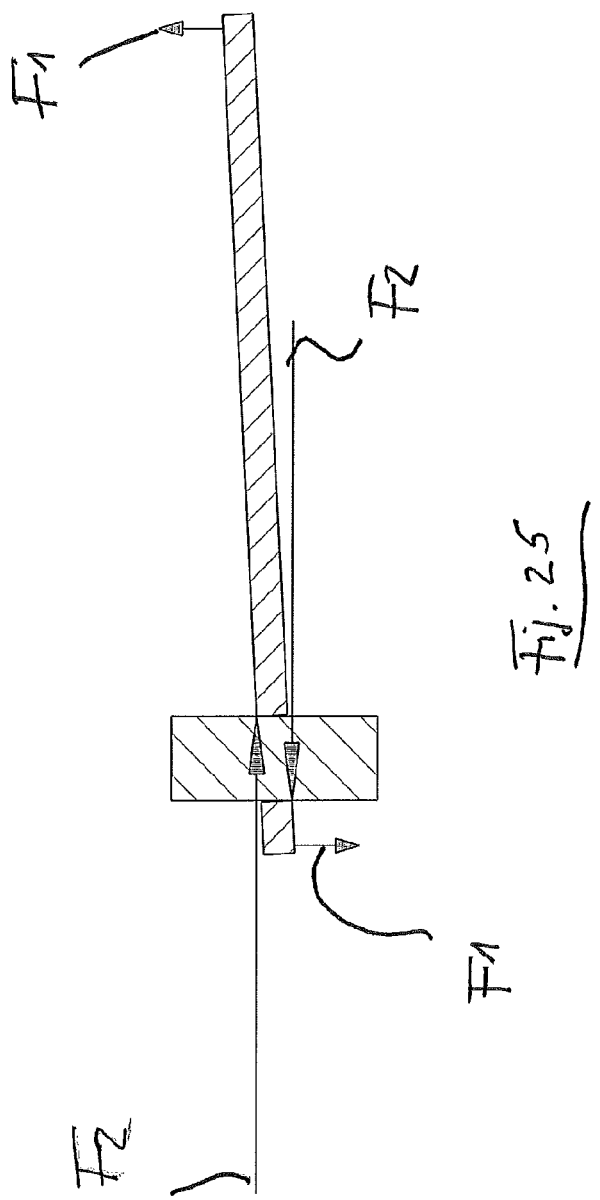
FIG. 25 shows in a schematic diagram the tilting while omitting snap-in tongues.

FIG. 25 shows in a schematic view, the tilting with omitted snap-in tongue 510.

Figure 26:
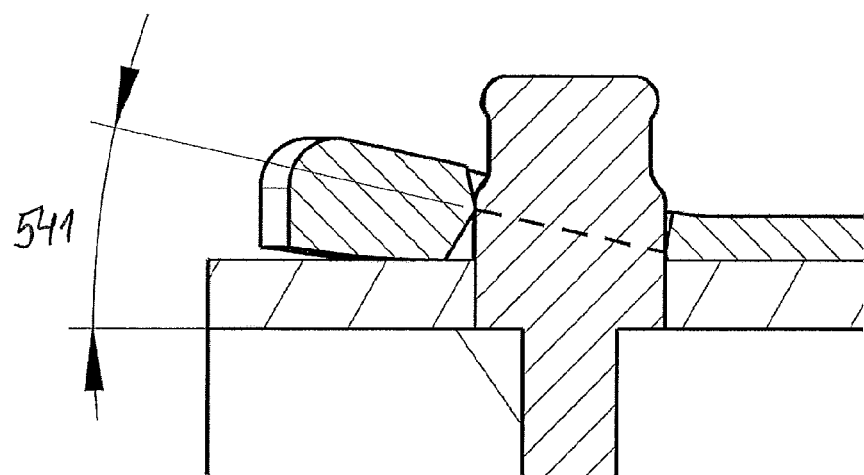
FIG. 26 shows in a schematic view, the first alignment device in the added position.

FIG. 26 shows in a schematic view, the first alignment device 504 in the equipped position.

Figure 27:
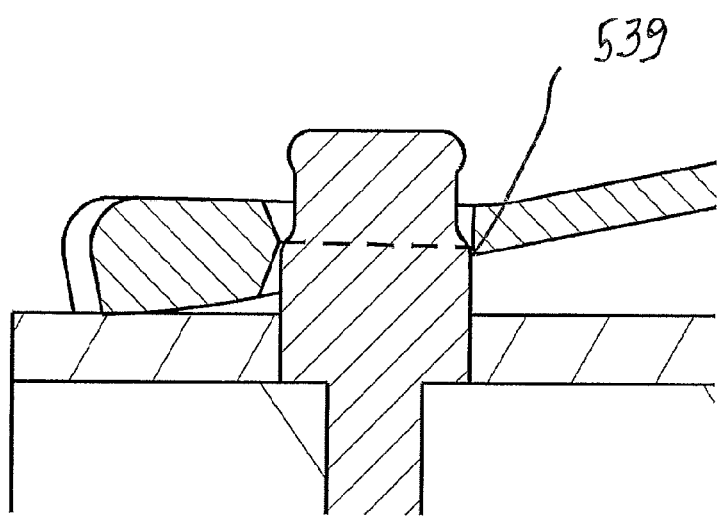
FIG. 27 shows in a schematic diagram the second alignment device in the critical moment of the unlatching.

FIG. 27 shows in a schematic view, the second alignment device 505 in the critical moment of unlatching.

Depending on the lifting edge distance 537 and the alignment height 523, the pitch angle 541 of the through-hole or opening of the first alignment device 504 is advantageously about 9 to 14°. Here, the moment of unlatching the snap-in tongues 510 substantially coincides with disengaging 539 the aligning facets 509 with the alignment diameter 522 of the alignment pins 517, 518, wherein the distance projected on the machine level of the two facets involved during the lifting-removal movement is continuously enlarged and remains always greater than the alignment diameter 522.

LIST OF REFERENCE NUMERALS 1000 blood treatment cassette, fluid cassette or cassette
1 hard part
3 film
502 chamber boundaries
503 edge bar
504 first alignment device
505 second alignment device
506 lifting edge bar
506a taper facet
506b rounded edge
506c front area
507 insertion chamfer or insertion funnel
508 closed edge bar
509 aligning facets
510 snap-in tongue
511 cuts
512 latching edge
514 actuator-sensor unit
515 actuator-sensor mat
516 actuator-sensor plate
517 first alignment pin
518 second alignment pin
519 transitions
520 edge of front area
521 snap-in diameter
522 alignment diameter
523 alignment height
524 machine door
525 support zone
526 support zone
527 line contact sections
528 rounded transition
530 lateral misalignment
531 lateral misalignment
532 maximum angle tilting
533 distance
534 angle tilting
535 angle area
536 angle area
537 lifting edge distance
538 tilt situation
539 tilt situation
540 pin or tongue
541 tilted arrangement
5000 machine or blood treatment apparatus

What is claimed is:

1. A blood treatment apparatus comprising:
an actuator-sensor plate comprising a surface configured to interface with and support a fluid cassette during use of the blood treatment apparatus, the actuator-sensor plate including at least one integrated actuator configured to interact with the fluid cassette while the fluid cassette is connected to the blood treatment apparatus;
a first alignment pin attached to the actuator-sensor plate and extending from the surface of the actuator-sensor plate; and
a second alignment pin attached to the actuator-sensor plate and extending from the surface of the actuator-sensor plate,
wherein the first alignment pin is configured to engage with a first alignment opening defined by the fluid cassette and the second alignment pin is configured to engage with a second alignment opening defined by the fluid cassette,
wherein the first alignment pin comprises:
an alignment diameter;
a snap-in diameter; and
a portion extending between the alignment diameter and the snap-in diameter,
wherein the alignment diameter: (i) is closer to the surface of the actuator-sensor plate than the snap-in diameter, (ii) is larger than the snap-in diameter, and (iii) is the largest diameter of the first alignment pin, and
wherein the portion of the first alignment pin extending between the alignment diameter and the snap-in diameter has a diameter that is less than each of the alignment diameter and the snap-in diameter.

2. The blood treatment apparatus according to claim 1, wherein the second alignment pin also comprises the alignment diameter and the snap-in diameter.

3. The blood treatment apparatus according to claim 2, wherein the first and second alignment pins are dimensionally alike each other.

4. The blood treatment apparatus according to claim 1, wherein the first and second alignment pins each extend perpendicularly to the actuator-sensor plate.

5. The blood treatment apparatus according to claim 1, wherein the first and second alignment pins are each rotationally symmetrical.

6. The blood treatment apparatus according to claim 1, wherein the actuator-sensor plate supports the fluid cassette on a portion of the actuator-sensor plate that is planar.

7. The blood treatment apparatus according to claim 1, further comprising a mat disposed on the actuator-sensor plate such that the fluid cassette rests on the mat while the fluid cassette is connected to the blood treatment apparatus.

8. The blood treatment apparatus according to claim 7, wherein the first and second alignment pins each extend through the mat.

9. The blood treatment apparatus according to claim 7, further comprising a door that can be closed to press the fluid cassette against the mat during the use of the blood treatment apparatus.

10. The blood treatment apparatus according to claim 9, wherein, while the door is closed, surfaces of the door that press against the fluid cassette are parallel to the actuator-sensor plate.

11. The blood treatment apparatus according to claim 1, wherein the first alignment pin has a rounded front peripheral edge.

12. The blood treatment apparatus according to claim 1, wherein a height of the alignment diameter portion of the first pin is within a range of 0.1 to 0.5 times of the alignment diameter.

13. The blood treatment apparatus according to claim 1, wherein the first alignment pin has a central flat front area.

* * * * *